United States Patent
Krueger et al.

(10) Patent No.: US 10,570,438 B2
(45) Date of Patent: *Feb. 25, 2020

(54) RAPID PEPTIDOGLYCAN-BASED ASSAY FOR DETECTION OF BACTERIAL CONTAMINATION

(71) Applicant: Immunetics, Inc., Marlborough, MA (US)

(72) Inventors: Neil X. Krueger, Roslindale, MA (US); Andrew Han, Cambridge, MA (US); Andrew E. Levin, Wellesley, MA (US); Victor Kovalenko, Saco, ME (US)

(73) Assignee: Immunetics, Inc., Marlborough, MA (US)

( * ) Notice: Subject to any disclaimer, the term of this patent is extended or adjusted under 35 U.S.C. 154(b) by 54 days.

This patent is subject to a terminal disclaimer.

(21) Appl. No.: 15/880,903

(22) Filed: Jan. 26, 2018

(65) Prior Publication Data

US 2018/0245127 A1 Aug. 30, 2018

Related U.S. Application Data

(63) Continuation of application No. 14/872,808, filed on Oct. 1, 2015, now Pat. No. 9,879,301, which is a continuation of application No. 14/096,468, filed on Dec. 4, 2013, now abandoned, which is a continuation of application No. 13/898,683, filed on May 21, 2013, now Pat. No. 8,841,086, which is a continuation of application No. 12/574,590, filed on Oct. 6, 2009, now Pat. No. 8,450,079, which is a continuation-in-part of application No. 11/413,977, filed on Apr. 28, 2006, now Pat. No. 7,598,054, which is a continuation-in-part of application No. PCT/US2004/035160, filed on Oct. 22, 2004.

(60) Provisional application No. 60/516,576, filed on Oct. 31, 2003.

(51) Int. Cl.
*C12Q 1/04* (2006.01)
*C12Q 1/26* (2006.01)
*G01N 21/25* (2006.01)
*C12Q 1/22* (2006.01)
*G01N 33/569* (2006.01)

(52) U.S. Cl.
CPC .............. *C12Q 1/26* (2013.01); *C12Q 1/04* (2013.01); *C12Q 1/22* (2013.01); *G01N 21/25* (2013.01); *G01N 21/255* (2013.01); *G01N 33/56911* (2013.01); *C12Q 2304/20* (2013.01); *G01N 2333/195* (2013.01); *G01N 2333/43552* (2013.01); *G01N 2333/90245* (2013.01); *G01N 2400/24* (2013.01); *G01N 2800/26* (2013.01)

(58) Field of Classification Search
None
See application file for complete search history.

(56) References Cited

U.S. PATENT DOCUMENTS

| | | |
|---|---|---|
| 4,054,415 A | 10/1977 | Seligson et al. |
| 4,158,545 A | 6/1979 | Yamashita et al. |
| 4,168,955 A | 9/1979 | Allington |
| 4,234,539 A | 11/1980 | Ginsberg et al. |
| 4,305,723 A | 12/1981 | Kolber et al. |
| RE31,150 E | 2/1983 | Ginsberg et al. |
| 4,383,041 A | 5/1983 | Kutsusawa et al. |
| 4,595,769 A | 6/1986 | D'Silva |
| 4,596,769 A | 6/1986 | Shockman et al. |
| 4,675,290 A | 6/1987 | Matsumoto et al. |
| 4,692,308 A | 9/1987 | Riley et al. |
| 4,908,186 A | 3/1990 | Sakamaki |
| 4,970,152 A | 11/1990 | Ashida et al. |
| 5,314,663 A | 5/1994 | Mimura |
| 5,316,911 A | 5/1994 | Baek et al. |
| 5,387,526 A | 2/1995 | Garner et al. |
| 5,563,031 A | 10/1996 | Yu |
| 5,585,248 A | 12/1996 | Ashida et al. |
| 5,710,012 A | 1/1998 | Nikolyukin et al. |
| 5,714,343 A | 2/1998 | Tuompo et al. |
| 5,747,277 A | 5/1998 | Tsuchiya |
| 5,917,592 A | 6/1999 | Skiffington |
| 5,962,765 A | 10/1999 | St.Leger et al. |
| 6,034,217 A | 3/2000 | Ashida et al. |
| 6,203,900 B1 | 3/2001 | Saika et al. |
| 6,274,565 B1 | 8/2001 | Katsumi |
| 6,284,885 B1 | 9/2001 | Tamura et al. |
| 6,306,577 B1 | 10/2001 | Tamura et al. |

(Continued)

FOREIGN PATENT DOCUMENTS

| | | |
|---|---|---|
| EP | 0757103 A2 | 2/1997 |
| JP | 7289251 | 11/1995 |

(Continued)

OTHER PUBLICATIONS

Abdullah, J. et al., Fabrication of an Optical Biosensor Based on Immobilized MBTH and Tyrosinase for Determination of Phenolic Compounds, 2005 Asian Conference on Sensors and the International Conference on new Techniques in Pharmaceutical andBiomedical Research, 103-106 (2005).

Arendt, A. et al., Fatal Bacterial Infections Associated with Platelet Transfusions—United States, 2004, MMWR, 54(07):168-170 (2005).

Ashida, M., A cane sugar factor suppressing activation of prophenoloxidase in haemolymph of the silkworm, *Bombyx mori*, Insect Biochemistry, 11:57-65 (1981).

Aubuchon, J.P., The Reliability of Bacterial Detection in Platelets, ISBT Science Series 1:59-63 (2006).

Beausang, L.A. et al., A Rapid Assay for the Detection of Bacteria in Platelet Units, poster presentation, American Association of Blood Banks meeting (2004).

(Continued)

*Primary Examiner* — Ralph J Gitomer

(74) *Attorney, Agent, or Firm* — Choate, Hall & Stewart LLP; Charles E. Lyon; Brian E. Reese

(57) ABSTRACT

The invention relates to a colorimetric method for detecting bacterial or fungal pathogens by detecting peptidoglycan or (1-3)-β-D-glucan in a sample.

17 Claims, 33 Drawing Sheets

(56) References Cited

U.S. PATENT DOCUMENTS

| | | | |
|---|---|---|---|
| 6,379,915 | B1 | 4/2002 | Douglas et al. |
| 6,413,729 | B1 | 7/2002 | Ashida et al. |
| 6,790,661 | B1 | 9/2004 | Goodnow |
| 6,987,002 | B2 | 1/2006 | Auh et al. |
| 7,598,054 | B2 * | 10/2009 | Kovalenko ............ C12Q 1/04 435/206 |
| 8,450,079 | B2 * | 5/2013 | Kovalenko ............ C12Q 1/04 435/25 |
| 8,841,086 | B2 * | 9/2014 | Han ........................ C12Q 1/04 435/25 |
| 9,879,301 | B2 * | 1/2018 | Krueger .................. C12Q 1/04 |
| 2004/0248271 | A1 | 12/2004 | Park et al. |
| 2006/0269982 | A1 | 11/2006 | Kovalenko et al. |
| 2006/0292662 | A1 | 12/2006 | Park et al. |
| 2010/0227353 | A1 | 9/2010 | Kovalenko et al. |
| 2014/0011218 | A1 | 1/2014 | Han et al. |
| 2014/0329304 | A1 | 11/2014 | Bodkin et al. |
| 2016/0201109 | A1 | 7/2016 | Bodkin et al. |

FOREIGN PATENT DOCUMENTS

| | | |
|---|---|---|
| JP | H11-290095 A | 10/1999 |
| JP | 3533699 B2 | 5/2004 |
| KR | 20020093612 A | 12/2002 |
| KR | 100485947 B1 | 4/2005 |
| WO | WO-8302123 A1 | 6/1983 |
| WO | WO-9931229 A2 | 6/1999 |
| WO | WO-01/18057 A2 | 3/2001 |
| WO | WO-01/52905 A1 | 7/2001 |
| WO | WO-02/16425 A1 | 2/2002 |
| WO | WO-0212526 A2 | 2/2002 |
| WO | WO-02/101083 A1 | 12/2002 |
| WO | WO-2005/045065 A1 | 5/2005 |
| WO | WO-2005093087 A1 | 10/2005 |
| WO | WO-2007127459 A2 | 11/2007 |
| WO | WO-2011/044234 A2 | 4/2011 |

OTHER PUBLICATIONS

Beausang, Lee Anne et al., Development of a Rapid Assay for the Detection of Bacteria in Platelet Units, powerpoint presentation, American Association of Blood Banks meeting (2003).

Besson Faure, I., Rapid screening for bacterial contamination of blood products, J. Lab Med 30(2):91-100 (2006).

Brecher, M. E. et al, Evaluation of a new generation of culture bottle using an automated bacterial culture system for detecting nine common contaminating organisms found in platelet components, Transfusion, 42(6): 774-779 (2002).

Brecher, M.E. et al., Antibotic-labeled probes and microvolume fluorimetry for the rapid detection of bacterial contamination in platelet components: a preliminary report, Transfusion, 40:411-413 (2000).

Brecher, M.E. et al., Bacterial Contamination of Blood Components, Clinical Microbiology Reviews, 195-204 (2005).

Brecher, M.E. et al., Evaluation of an automated culture system for detecting bacterial contamination of platelets: an analysis with 15 contaminating organisms, Transfusion, 41:477-482 (2001).

Brecher, M.E. et al., Growth of bacteria in inoculated platelets: implications for bacteria detection and the extension of platelet storage, Transfusion, 40:1308-1312 (2000).

Brecher, M.E. et al., Platelet bacterial contamination and the use of a chemiluninescence-linked universal bacterial ribosomal RNA gene probe, Transfusion, 34:750-755 (1994).

Brecher, M.E. et al., The use of a chemiluminescence-linked universal bacterial ribosomal RNA gene probe and blood gas analysis for the rapid detection of bacterial contamination in white cell-reduced and nonreduced platelets, Transfusion,33:450-457 (1993).

Burns, K.H. et al., Bacterial Contamination of Platelet Units, Arch Pathal Lab Med, 128:279-281 (2004).

David Kagan and Andrew E. Levin, Rapid Assay for Bacterial Contamination of Platelets, powerpoint presentation, American Association of Blood Banks meeting, Oct. 16, 2001.

Heal, J.M. et al., Bacterial proliferation in platelet concentrates, Transfusion, 26(40):388-390 (1986).

Hillyer, C.D. et al., Bacterial Contamination of Blood Components: Risks, Strategies, and Regulation, Hematology, 575-589 (2003).

Inada, K. et al., A Silkworm Larvae Plasma Test for Detecting Peptidoglycan in Cerebrospinal Fluid is Useful for the Diagnosis of Bacterial Meningitis, Microbiol. Immunol., 47(10):701-707 (2003).

International Search Report for PCT/US2010/051627 dated Jun. 23, 2011.

International Search Report from PCT/US04/35160, 2 pages, dated Apr. 25, 2005.

International Search Report from PCT/US07/10397 dated Mar. 14, 2008.

Jacobs, M.R. and Yomaovian, R., Bacterial Contamination of Platelets, Experience at University Hospitals of Cleveland, 1991-2005, FDA presentation (2006).

Jacobs, M.R. et al., Relationship between Bacterial Load, Species Virulence, and Transfusion Reaction withy Transfusion of Bacterially Contaminated Platelets, CID, 46:1214-1220 (2008).

Ji, C. et al., A Pattern Recognition Serine Proteinase Triggers the Prophenoloxidase Activation Cascade in the Tobacco Hornworm, Manduca sexta, The J. of Biological Chemistry, 279(33):34101-34106 (2004).

Jiang, H. et al., Proteolytic Activation of Prophenoloxidase in an Insect Manduca sexta, Phylogenetic Perspectives on the Vertebrate Immune System, 313-317 (2001).

Johansson, M.W. et al., The Prophenoloxidase Activating System and Associated Proteins in Invertebrates, Prog Mol Subcell Biol.;15:46-66 (1996).

Kagan, D. et al, Rapid Assay for Bacterial Contamination of Platelets, powerpoint presentation, American Association of Blood Banks meeting, Oct. 16, 2001.

Kanost, M.R. et al., Innate immune responses of a lepidopteran insect, Manduca sexta, Immunological Reviews 198:97-105 (2004).

Kaufman, R.M., Platelets: Testing, Dosing and the Storage Lesion-Recent Advances, American Society of Hematology, pp. 492-496 (2006).

Kirby, C. et al., BacTx—A Rapid Assay for the Detection of Bacteria in Platelet Units, poster presentation, American Association of Blood Banks meeting (2005).

Klouche, M., Concepts to ascertain bacterial safety of blood products—Screening methods to detect bacterial contamination Part 1, J Lab Med 30(2):58-59 (2006).

Kobayashi, T. et al., Detection of Peptidoglycan in Human Plasma Using the Silkworm Larvae Plasma Test, FEMS Immunology and Medical Microbiology, 28:49-53 (2000).

Kocoglu, M.E. et al., Evaluation of Negative Results of BacT/Alert 3D Automated Blood Culture System, The J. of Microbiology, 43(3):257-259 (2005).

Krueger, N. X. et al., BacTx Assay for Bacterial Contamination of Platelets Detects Bacteria Missed by Automated Culture Systems, poster presentation, American Association of Blood Banks meeting (2008).

Larsen, C.P. et al., Six years' experience of using the BacT/ALERT system to screen all platelet concentrates, and additional testing of outdated platelet concentrates to estimate the frequency of false-negative results, Vox Sanguinis, 88:93-97(2005).

Levin, A.E. et al., Kinetic Assay for Bacterial Contamination of Platelets Accelerates Detection, poster presentation, American Association of Blood Banks meeting (2007).

Liu, C. et al., Mammalian Peptidoglycan Recognition Protein Binds Peptidoglycan with High Affinity, Is Expressed in Neutrophils, and Inhibits Bacterial Growth, The J. of Biological Chemistry, 275(32):24490-24499 (2000).

Mcdonald, C.P. et al., Pall eBDS: an enhanced bacterial detection system for screening platelet concentrates, Transfusion Medicine, 15:259-268 (2005).

Mohammadi, T. et al., Optimal Sampling time after preparation of platelet concentrates for detection of bacterial contamination by quantitative real-time polymerase chain reaction, Vox Sanguinis, 89:208-214 (2005).

Mohr, H. et al., Basics of flow cytometry-based sterility testing of platelet concentrates, Transfusion, 46:41-49 (2006).

(56) References Cited

OTHER PUBLICATIONS

Mohr, H. et al., Sterility testing of platelet concentrates prepared from deliberately infected blood donations, Transfusion, 46:486-491 (2006).
Muller, T.H. et al., Methods for the detection of bacterial contamination in blood products, J Lab Med 30(2):74-90 (2006).
Myhre, B.A. et al., Bacteriocidal Properties of Platelet Concentrates, Transfusion, 14(2):116-123 (1974).
Nellaiappan, K. et al., A Method for Demonstrating Prophenoloxidase after Electrophoresis, Biotechnic & Histochemistry, 68(4):193-195 (1993).
Palavecino, E.L. et al., Detecting Bacterial Contamination in Platelet Products, Clin. Lab. 52:443-456 (2006).
Punsalang, A. et al., Growth of gram-positive and gram-negative bacteria in platelet concentrates, Transfusion, 29:596-599 (1989).
Ramirez-Arcos, S. et al., Evaluation of pooled cultures for bacterial detection in whole blood-derived platelets, Transfusion, 45:1275-1279 (2005).
Rodrigues-Lopez J. et al., A Continuous Spectrophotometric Method for the Determination of Monophenolase Activity of Tyrosinase Using MBTH, Analytical Biochemistry 216, 205-212 (1994).
Satoh, D. et al., Prophenoloxidase-activating Enzyme of the Silkworm, *Bombyx mori*, The J. of Biological Chemistry, 274(11):7441-7453 (1999).
Saul, S.J. et al., Protease Mediated Prophenoloxidase Activation in the Hemolymph of the Tobacco Hornworm, *Manduca sexta*, Archives of Insect Biochemistry and Physiology, 5:1-11 (1987).
Schmidt, M. et al., Optimized Scansystem.TM. platelet kit for bacterial detection with enhanced sensitivity: detection within 24 h after spiking, Vox Sanguinis, 89:135-139 (2005).
Seaver, M. et al., First results using automated epifluorescence microscopy to detect *Escherichia coli* and *Staphylococcus epidermidis* in WBC-reduced platelet concentrates, Transfusion, 41:1351-1355 (2001).
Shulman, I.A. et al., College of American Pathologists Laboratory Accreditation Checklist item TRM.44955, Arch Pathol Lab Med, 128:958-963 (2004).
Soderhall et al., Role of the prophenoloxidase-activating system in invertebrate immunity, Opinion in Immunology, 10:23-28 (1998).
Stormer, M. et al., Detection of bacteria in platelet concentrates prepared from spiked single donations using cultural and molecular genetic methods, Transfusion Medicine, 17:6170 (2007).

Supplemental EP Search Report for Application No. 108226602.8 dated May 13, 2013.
Supplementary European Search Report from EP 04 79 6195 dated Aug. 14, 2007.
Supplementary European Search Report from EP 04 79 6195 dated Sep. 20, 2007.
Takehana, A. et al., Overexpression of a pattern-recognition receptor, peptidoglycan-recognition protein-LE, activates imd/relish-mediated antibacterial defense and the prophenoloxidase cascade in *Drosophila* larvae, PNAS, 99(21):13705-13710(2002).
Tsuchida, K. et al., Detection of Peptiodoglycan and endotoxin in dialysate, using silkworm larvae plasma and limulus amebocyte lysate methods, Nephron., 75(4):438-443 (1997).
Tsuchiya, M. et al., Detection of Peptidoglycan and Beta-Glucan with Silkworm Larvae Plasma Test. FEMS Immunology and Medical Microbiology 15(2-3)129-134,Sep. 1996.
Wagner, S.J. et al., Comparison of bacteria growth in single and pooled platelet concentrates after deliberate inoculation and storage, Transfusion, 35:298-302 (1995).
Wagner, S.J. et al., Evaluation of an automated microbiologic blood culture device for detection of bacteria in platelet components, Transfusion, 38:674-679 (1998).
Wako, SLP-HS Single Reagent Set, Product Insert, Rev. Mar. 2002.
Walther-Wenke, G., Bacterial contamination of blood components—incidence and significance for homologous and autologous transfusion, J. Lab Med 30(2):66-73 (2006).
Winder, A, A Stopped Spectrophotometric Assay for the Dopa Oxidase Activity of Tyrosinase, J. Biochem. Biophys Methods, 28(3)173-183 (1994).
Written Opinion for PCT/US07/10397, 3 pages (dated Mar. 14, 2008).
Written Opinion for PCT/US2004/035160, 5 pages, dated Mar. 29, 2005.
Written Opinion for PCT/US2010/051627, 4 pages (dated Jun. 23, 2011).
Yazer, M.H. et al., Use of a pH meter for bacterial screening of whole blood platelets, Transfusion, 45:1133-1137 (2005).
Yomtovian, R.A. et al., Evolution of surveillance methods for detection of bacterial contamination of platelets in a university hospital, 1991 through 2004, Transfusion, 46:719-730 (2006).
Yoshida, H. et al., .beta.-1,3-Glucan Receptor and peptidoglycan receptor are present as separate entities within insect prophenoloxidase activating system, Biochemical and Biophysical Research Communications, 141(3):1177-1184 (1986).

\* cited by examiner

Experiment 2.

A:

B:

RAPID PEPTIDOGLYCAN-BASED ASSAY FOR DETECTION OF BACTERIAL CONTAMINATION

CROSS-REFERENCE TO RELATED APPLICATIONS

This application is a continuation of Ser. No. 14/872,808 filed on Oct. 1, 2015, now U.S. Pat. No. 9,879,301; which is a continuation of Ser. No. 14/096,468 filed Dec. 4, 2013, which is a continuation of Ser. No. 13/898,683 filed May 21, 2013, now U.S. Pat. No. 8,841,086; which is a continuation of Ser. No. 12/574,590 filed Oct. 6, 2009, now U.S. Pat. No. 8,450,079; which is a continuation-in-part of U.S. application Ser. No. 11/413,977, filed Apr. 28, 2006, now U.S. Pat. No. 7,598,054; which is a continuation-in-part of International Application No. PCT/US2004/035160, filed Oct. 22, 2004, which claims the benefit of U.S. Provisional Application Ser. No. 60/516,576, filed Oct. 31, 2003. The entire contents of each of these applications are hereby expressly incorporated herein by reference.

GOVERNMENT SUPPORT

This invention was made with government support under grant No. HL65877 awarded by the National Heart, Lung and Blood Institute. The government may have certain rights in the invention.

FIELD OF THE INVENTION

This invention relates to a colorimetric assay and method for rapidly and easily detecting the presence of a bacterial or fungal pathogen in a sample.

BACKGROUND OF THE INVENTION

On Mar. 1, 2004, American Association of Blood Banks (AABB) standards mandated that United States blood centers commence testing all platelet units for bacterial contamination. This new standard was based on the significant risks to transfusion patients associated with contaminated platelet units. Approximately 4 million platelet units are transfused per year in the U.S., of which up to 4000 are potentially contaminated. Contaminated platelet units have been identified as a cause of sepsis-related morbidity and mortality. The room temperature storage requirement of platelets, which is essential for viability and function, also serves to facilitate bacterial growth. Even at early time points in the mandatory maximum five-day storage time limit post-collection, microbial growth may reach significant levels. Further, it may be desirable to monitor platelet units for fungal contamination in addition to bacterial contamination.

Furthermore, there exists no assay for direct detection of bacteria in urine for diagnosis of urinary tract infections (UTIs). Current methods instead diagnose UTIs indirectly by urinalysis, for example, by determining specifically the presence of nitrites, leukocytes, or leukocyte esterase and chemical testing for glucose or pH. Diagnosis of a UTI, if confirmed, is done so by bacterial culture, which can be laborious and time consuming. Similarly, there is no direct test for bacteria in cerebrospinal fluid available which could be used for the rapid diagnosis of bacterial meningitis, a rapidly progressing infection of the central nervous system which is typically fatal if antibiotic treatment is not initiated promptly. Culture methods are too slow to be of use in diagnosing such infections.

The need to detect bacterial and fungal contamination, however, is not limited to platelet units, urine, and cerebrospinal fluid. Bacterial and fungal contamination of many clinical, agricultural or environmental products may lead to severe illness, and even death, if contacted by a subject or administered to a subject. In addition to monitoring clinical products such as blood, plasma, platelets, and other bodily fluids such as urine and cerebrospinal fluid for bacterial and/or fungal contamination in a hospital or clinical setting, it is highly desirable to monitor wound dressings for contamination in remote or field locations. Also, there are increasing safety concerns to monitor both food products and the water supply for bacterial and fungal contamination. This concern may also apply to recreational facilities such as swimming pools and lakes, which may be contaminated with high levels of bacteria or fungi. Accordingly, there is an immediate and unmet need for detecting bacterial or fungal contamination in numerous products that are consumed or used by humans.

Many tests exist for sensitive detection of a broad spectrum of various bacterial species based on the detection of specific bacterial antigens. One limitation of these methods is that they cannot be applied directly for testing of samples where the spectrum of bacterial pathogens is unknown. There remains a need for the development of a test capable of detecting all bacteria present irrespective of species or strain.

Current tests for bacterial and/or fungal contamination involve complicated tasks requiring particular reaction conditions and often take days to complete. Another barrier to widespread acceptance of various tests for bacterial or fungal contamination is low sensitivity, low specificity, and high cost. For example, conventional culture methods require culturing or growing the bacteria on a petri dish and then determining the type of bacteria by Gram staining. This process can often take up to 72 hours. A quick and easy assay for detecting bacterial or fungal contamination is needed and as such would facilitate a ready supply of clinical, agricultural, and environmental products that are free of bacterial and fungal contamination and safe for use by humans.

SUMMARY OF THE INVENTION

To address this need, with specific application to ensuring the safety of platelets for transfusion and for the diagnosis of UTI and bacterial infection of the central nervous system, we have developed a rapid, sensitive, and specific assay for the detection of bacteria in samples such as platelet units, urine urine, and cerebrospinal fluid (CSF) samples. The assay is based on the detection of peptidoglycan, a cell wall component of all bacteria. Present in both Gram-negative and Gram-positive bacteria, peptidoglycan can be used to detect bacterial species known as human pathogens and as frequent contaminants of platelet units as well as less common contaminants or slow growing bacterial pathogens. Further, since peptidoglycan is a major structural component of the cell wall it can be easily and rapidly detected in bacterial populations. The assay may also be used to detect β-glucan, a cell wall component of true fungi, such as yeast and molds.

In one aspect, the present invention features a rapid, easy, and sensitive method for detecting peptidoglycan (PG) in a sample using a prophenoloxidase cascade system (POC) that forms a red-colored reaction product in the presence of PG.

The presence of the red-colored reaction product may be determined rapidly, such as in less than one hour, and easily, such as by visual inspection or spectrophotometrically. In exemplary embodiments, the red-colored reaction product is generated when quinones produced from oxidized substrates of phenoloxidase (PO) react with 3-methyl-2-benzothiozolinone hydrazone (MBTH) or a derivative thereof. In a further embodiment, the detection of PG in platelets and other clinical samples may be enhanced by alkaline extraction at an elevated temperature with subsequent neutralization. In a further embodiment, alkaline extraction is used as an efficient approach for the inactivation of various inhibitory factors, which may be present in the plasma or plasma fraction of platelet preparations and in other clinical samples such as urine and cerebrospinal fluid. In a still further embodiment, alkaline extraction is used for the solubilization of platelet cells, which permits large amounts of platelets in samples to be tested, thus increasing the assay sensitivity.

Further, the PG may be detected at levels corresponding to contaminating concentrations of bacteria. For instance, PG can be detected at concentrations of less than 125 pg/ml. In an exemplary embodiment, the PG originates from bacteria found in the sample. The PG may be shed from bacterial cells, or present in the intact cell wall. Alternatively, the detection assay described herein may be used to detect β-1,3-glucan, a cell wall component of fungi. Further, in the detection assay described herein, the PO may be obtained from the plasma, hemolymph, or cuticle of the body wall of insect larvae, from the Lepidoptera order (such as *Manduca sexta* (tobacco hornworm), *Manduca quinquemaculata* (tomato hornworm), *Gelleria melonella*, *Hyalphoma ceropia*, *Bombyx mori* (silkworm)), Diptera order (such as *Sarcophaga peregrina* (flesh fly), *Sarcophaga mucosa*, *Mucsa domestica* (house fly)), Orthoptera order (such as *Locusta migratoria*, *Teleogryllus* (e.g., Emmafield cricket), Coleoptera order (beetles) (such as *Cerambyx* and *Acalolepa luxuriosa*).

In certain embodiments, the present invention features a method for detecting peptidoglycan or β-glucan in a sample comprising (a) incubating the sample with a prophenoloxidase cascade system, a phenoloxidase substrate that generates a quinone reaction product, and 3-methyl-2-benzothiazolinone hydrazone (MBTH) or derivative thereof; and, (b) detecting the formation of a colored prophenoloxidase reaction product, wherein formation of the reaction product indicates the presence of peptidoglycan or β-1,3-glucan in the sample. In exemplary embodiments, the formation of the reaction product indicates the presence of bacteria or fungi in the sample.

In further embodiments, the sample is a clinical sample, an environmental sample, an agricultural sample, a medical product, or a manufacturing sample. A clinical sample may be a urine sample, hydration fluid, nutrient fluid, blood, blood product, cerebrospinal fluid (CSF), tissue extract, vaccine, anesthetic, pharmacologically active agent, dialysis fluid, or an imaging agent. The clinical sample may comprise platelets. The colorimetric assay methods may also be used to detect the presence of bacteria or fungi in medical devices (such as catheters, stents, IVs), agricultural specimens (such as food and water), environmental specimens (such as lakes or pools), and manufacturing samples (such as the machinery for processing samples). In certain embodiments, the sample may be a suspension or a liquid. In further embodiments, the sample may be processed by centrifugation and bacteria or fungi present in the sample may be pelleted during centrifugation. Other means of concentrating the bacteria or fungi may also be used (e.g., filtration).

In further embodiments, the method for detecting peptidoglycan or β-glucan in a sample may comprise a prophenoloxidase cascade system that comprises prophenoloxidase activating enzyme, prophenoloxidase, and a serine proteinase cascade. The prophenoloxidase system may be obtained from insect plasma or hemolymph, and in exemplary embodiments, is obtained from silkworm larvae plasma. The prophenoloxidase cascade system from silkworm larvae plasma represents a complete system comprising many components. While many of the components of the prophenoloxidase cascade system are known, additional components may still be identified. The prophenoloxidase cascade system may further comprise a peptidoglycan binding protein. Alternatively, the prophenoloxidase cascade system may further comprise a β-glucan binding protein. In certain embodiments, the prophenoloxidase cascade system may further comprise both peptidoglycan binding protein and β-glucan binding protein. In further embodiments, the method for detecting peptidoglycan or β-glucan in a sample may comprise a phenoloxidase substrate that generates a quinone reaction product. The phenoloxidase substrate that generates a quinone reaction product may be L-3,4-dihydroxyphenylalanine, dopamine or other dihydroxyphenols or monophenols.

In still further embodiments, the method for detecting peptidoglycan or β-glucan in a sample may comprise the step of exposing the sample to an extraction solution, preferably at an elevated temperature, prior to incubating the sample with the prophenoloxidase cascade system, and subsequently the phenoloxidase substrate that generates a quinone reaction product that can react with 3-methyl-2-benzothiazolinone hydrazone or a derivative thereof. The extraction solution may be an alkaline extraction solution. The method for detecting peptidoglycan or β-glucan in a sample may also comprise the step of exposing the sample to a neutralization buffer prior to incubating the sample with the prophenoloxidase cascade system, the phenoloxidase substrate that generates a quinone reaction product, and 3-methyl-2-benzothiazolinone hydrazone or derivative thereof. Alternatively, the 3-methyl-2-benzothiazolinone or derivative thereof may be dissolved in the neutralization buffer. In another alternative, the 3-methyl-2-benzothiazolinone or derivative thereof may be lyophilized with the prophenoloxidase cascade system, including the phenoloxidase substrate that generates a quinone reaction product, to form a dry detection reagent that may be added to the sample after neutralizing the sample with neutralization buffer. The method described herein may still further comprise the step of exposing the sample to a stop reagent, wherein the stop reagent may be an acid reagent; a phenoloxidase specific inhibitor (e.g., phenyl-thiourea), or a strong anionic detergent (e.g., lithium or sodium salt of dodecylsulfate) alone or in combination with a phenoloxidase specific inhibitor. Alternatively, the conversion of phenoloxidase substrate to chromogenic product can be monitored continuously in a spectrophotometer, rather than stopping the reaction with a stop reagent at a specific time.

In another aspect, the present invention features a method for detecting peptidoglycan in a sample comprising (a) extracting the sample in an alkaline extraction solution, (b) incubating the sample with silkworm plasma larva, L-3,4-dihydroxyphenylalanine, and 3-methyl-2-benzothiazolinone hydrazone or derivative thereof, (c) stopping the reaction with phenyl-thiourea, and (d) detecting the formation of a colored prophenoloxidase reaction product, wherein the formation of the reaction product indicates the presence of peptidoglycan in the sample. Optionally, MBTH or derivative thereof is dissolved in a neutralization buffer and is added prior to the other components in step (b). Alternatively, neutralization buffer is added after step (a) and followed by the addition of a neutralized sample to a dry detection reagent containing MBTH or derivative thereof that has been co-lyophilized with silkworm plasma larva, L-3,4-dihydroxyphenylalanine. In addition, the conversion of phenoloxidase substrate to chromogenic product can be monitored continuously in a spectrophotomer, rather than stopping the reaction with a stop reagent at a specific time.

In another aspect, the present invention features a method for detecting β-glucan in a sample comprising (a) extracting the sample in an alkaline extraction solution, (b) incubating the sample with silkworm larvae plasma, L-3,4-dihydroxyphenylalanine, and 3-methyl-2-benzothiazolinone hydrazone or derivative thereof, (c) stopping the reaction with phenyl-thiourea, and (d) detecting the formation of a colored prophenoloxidase reaction product, wherein the formation of the reaction product indicates the presence of β-glucan in the sample. Optionally, MBTH or derivative thereof is dissolved in a neutralization buffer and is added prior to the other components in step (b). Alternatively, neutralization buffer is added after step (a) and followed by the addition of a dry detection reagent containing MBTH or derivative thereof that has been co-lyophilized with silkworm plasma larva, L-3,4-dihydroxyphenylalanine. In addition, the conversion of phenoloxidase substrate to chromogenic product can be monitored continuously in a spectrophotometer, rather than stopping the reaction with a stop reagent at a specific time.

In another aspect, the present invention features a kit for the rapid, easy, and sensitive detection of peptidoglycan in a sample. A kit for detecting peptidoglycan in a sample may comprise a prophenoloxidase cascade system, a phenoloxidase substrate that generates a quinone reaction product, and 3-methyl-2-benzothiazolinone hydrazone or derivative thereof. The prophenoloxidase cascade system is obtained from insect plasma or hemolymph, and in exemplary embodiments, is obtained from silkworm larvae plasma. The prophenoloxidase cascade system used in the kit comprises prophenoloxidase activating enzyme, prophenoloxidase, and a serine proteinase cascade. The kit may further comprise a peptidoglycan binding protein. The phenoloxidase substrate that generates a quinone reaction product provided in the kit may be L-3,4-dihydroxyphenylalanine (DOPA), dopamine, or another mono- or dihydroxy-phenolic compound. The kit may further comprise a peptidoglycan standard, wherein the peptidoglycan standard is isolated bacterial peptidoglycan, whole bacterial extract, or inactivated whole bacteria. Still further, the kit may comprise an extraction solution, such as an alkaline extraction solution. The kit may also comprise a neutralization buffer with or without MBTH or derivative thereof dissolved in a neutralization buffer. Where the kit comprises a neutralization buffer without MBTH or derivative thereof dissolved therein. The kit may further comprise a dry detection reagent containing MBTH or a derivative thereof co-lyophilized with a prophenoloxidase cascade system and a phenoloxidase substrate that generates a quinone reaction product. Optionally, the kit may further comprise a stop reagent, wherein the stop reagent is an acid reagent (e.g., tricholoracetic acid, perchloric acid, or tungstosilicic acid), an inhibitor of phenoloxidase (e.g., phenyl-thiourea), or a strong anionic detergent in sodium or lithium salt forms (dodecylsulphate or laurylsarcosine) alone or in combination with a phenoloxidase specific inhibitor. The kit may still further comprise instructions for spectrophotometric detection or a color-coded scale for visual evaluation as well as a sterile sample tube for performing the reaction. Optionally, the kit may also include a photometer for continuously monitoring the phenoloxidase substrate conversion reaction.

In another aspect, the present invention features a kit for the rapid, easy, and sensitive detection of β-glucan in a sample. A kit for detecting β-glucan in a sample may comprise a prophenoloxidase cascade system, a phenoloxidase substrate that generates a quinone reaction product, and 3-methyl-2-benzothiazolinone hydrazone or derivative thereof. The prophenoloxidase cascade system is obtained from insect plasma or hemolymph, and in exemplary embodiments, is obtained from silkworm larvae plasma. The prophenoloxidase cascade system used in the kit comprises prophenoloxidase activating enzyme, prophenoloxidase, and a serine proteinase cascade. The kit may further comprise a β-glucan binding protein. The phenoloxidase substrate that generates a quinone reaction product provided in the kit may be L-3,4-dihydroxyphenylalanine (DOPA), dopamine, or another mono- or dihydroxy-phenolic compounds. The kit may further comprise a β-glucan standard, wherein the β-glucan standard is isolated fungal β-glucan, whole fungal extract, or inactivated whole fungus. Still further, the kit may comprise an extraction solution, such as an alkaline extraction solution. The kit may also comprise a neutralization buffer with or without MBTH or a derivative thereof dissolved in a neutralization buffer. The kit may further comprise a dry detection reagent containing MBTH or derivative thereof co-lyophilized with a prophenoloxidase cascade system and a phenoloxidase substrate that generates a quinone reaction product. The kit may further comprise a stop reagent, wherein the stop reagent is an acid reagent (e.g., tricholoracetic acid, perchloric acid, or tungstosilicic acid), an inhibitor of phenoloxidase (e.g., phenyl-thiourea) or a strong anionic detergent (e.g., dodecylsulfate) alone or in combination with a phenoloxidase specific inhibitor. The kit may still further comprise instructions for spectrophotometric detection or a color-coded scale for visual evaluation as well as a sterile sample tube for performing the reaction.

There are many other applications of our invention, which will be readily apparent to the skilled artisan and are intended to be embraced within the scope of this disclosure.

DETAILED DESCRIPTION

1. General

Figure 1:
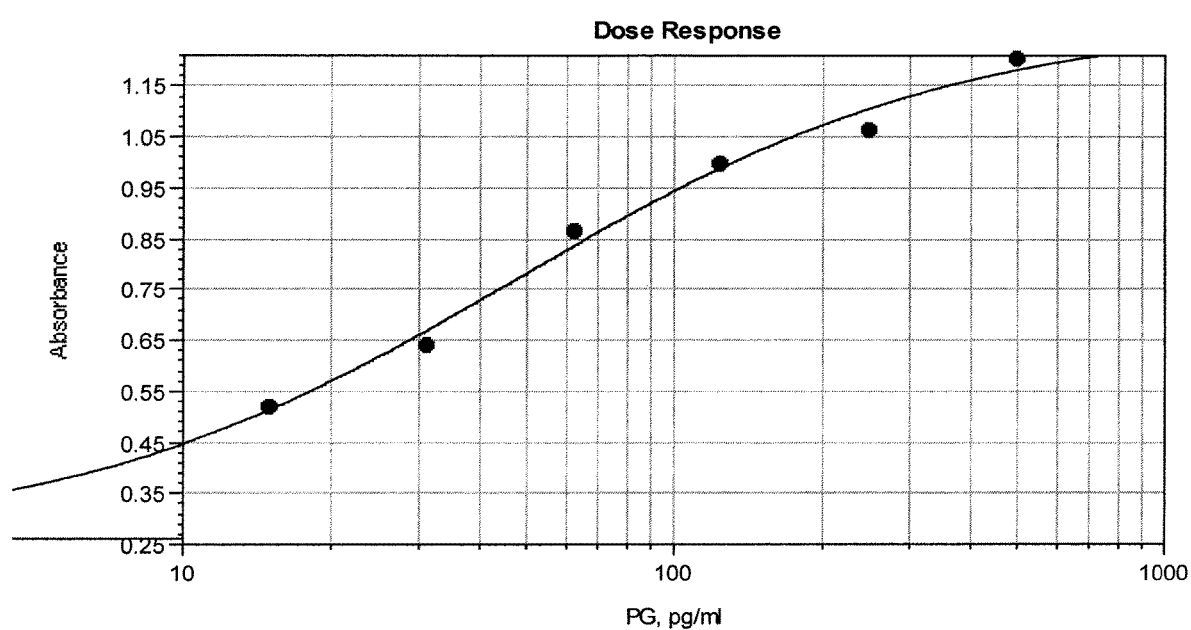
FIG. 1 is a graph showing a peptidoglycan dose response curve. The curve is represented by the equation $y=((A-D)/1+(x/C)^B))+D$, where A=0.258, B=0.958, C=47.511 and D=1.276; the $R^2$ value is 0.993.

Implementation of the AABB requirement to screen platelet units for bacteria requires the development and validation of tests suitable for this application. Ideally, sensitive detection of both Gram-positive and Gram-negative organisms will be combined with a short turnaround time, which maximizes the availability of platelet units. While culture-based methods have been the gold standard for detection of bacteria, offering high sensitivity, these methods are at the cost of turnaround time measured in hours to days.

Provided herein is a new assay for screening platelet units for bacterial contamination based on the direct detection of peptidoglycan, a component of both Gram-positive and Gram-negative bacteria. The assay described herein provides significant advances over assays that are currently available. First, the assay has been shown to detect a range of Gram-positive and Gram-negative species known as common contaminants of platelets at densities as low as 100 colony forming units (CFU)/ml. Moreover, the assay can detect slow-growing strains such as *S. epidermidis* in platelet units inoculated at very low density, in simulation of an actual contamination event, but in less than 7 hours from inoculation, vs. greater than 19 hours as reported for a current automated culture method (Brecher et al., Transfusion 41: 477-482 (2001)). Further, the assay requires no dedicated or sophisticated instrumentation and can be carried out with basic laboratory equipment. The assay can be applied to a single unit or batch testing. Accordingly, the results can be read visually for speed and simplicity or a plate reader may be used for quantitation, at equivalent sensitivity. With an approximate one-hour turnaround time, the assay may be useful for testing platelet units prior to release as well as in storage. It may also be potentially useful in monitoring the safety of platelets stored beyond the current 5 day maximum, and ultimately may extend the viability of stored platelet units.

Further, the assay results may be interpreted either qualitatively or quantitatively, with color development proportional to peptidoglycan concentration. Sensitivity was studied, as described below, with several bacterial species known to be frequent contaminants of platelet units including Gram-negative bacteria *S. marcescens, E. coli*, and *P. aeruginosa*, and Gram-positive *S. epidermidis*, which is a common, but relatively slow growing pathogen. In initial experiments, the proof of principle of sample treatment was established by measuring bacterial peptidoglycan in platelets collected by centrifugation from platelet preparation diluted with water. In these experiments, however, substantial interference from hemoglobin, which absorbs at 490 nm, was observed. To overcome the potential negative impact of hemoglobin interference as well as other inhibitory factors, which may be present in plasma, on the sensitivity of the assay, the assay described herein was further improved through an extraction procedure, which clarified the platelet suspension, eliminating interference in reading the result. An alkaline extraction procedure was implemented in the assay described herein and efficiently eliminates the activity of inhibitory factors. Further, alkaline extraction permits the use of large amounts of platelets in a concentrated form for testing, and thus, increased the sensitivity of the assay. Extraction also increased the release of peptidoglycan from bacteria in a form, which additionally enhanced detection resulting in up to 10-fold higher assay sensitivity. The assay described herein overcomes numerous factors that have made detection of bacterial contamination in platelets more difficult than the detection of bacterial contamination in plasma and other biological fluids that do not contain large amounts of various cells.

2. Definitions

The term "β-glucan" as used herein refers to β-1,3-glucan, a cell wall component of true fungi such as yeast and mold and a major polysaccharide component of fruit bodies of many basidiomycetes.

The term "hemolymph" as used herein refers to body fluid or plasma obtained from the body cavity of an insect.

The term "peptidoglycan" as used herein refers to a glycopeptide polymer that is a component of bacterial cell walls, including Gram-positive and Gram-negative bacteria. Peptidoglycan is generally characterized as containing N-acetyl- or N-glycolylmuramic acid and D-amino acids.

The term "prophenoloxidase cascade system" or "proPOC system" as used herein refers to a serine proteinase cascade system that is present in the hemolymph and cuticle of the body wall of insects. A prophenoloxidase cascade system comprises a prophenoloxidase activating enzyme, prophenoloxidase, and a serine proteinase cascade. A proPOC system may further comprise a peptidoglycan-binding protein(s) (PGBP) and/or a β-glucan-binding protein(s) (BGBP). The prophenoloxidase cascade system may additionally comprise components that remain to be identified. The prophenoloxidase cascade system from silkworm larvae plasma, however, represents a complete prophenoloxidase cascade system. In nature, the prophenoloxidase cascade system is one of the immune mechanisms in insects and is triggered by injury or minute amounts of peptidoglycan or β-glucan. Activation of the cascade begins from a specific recognition of PG or β-1,3-glucan with a corresponding PGBP or BGPB. These specific complexes trigger a serine protease cascade which activates prophenoloxidase activating enzyme, a specific protease, which in turn activates prophenoloxidase through cleavage of an N-terminal portion of this enzyme, which generates phenoloxidase, the active form. Active phenoloxidase catalyzes two reactions: 1) the oxygenation of monophenols to o-diphenols and 2) the oxidation of o-diphenols to quinones. Quinones produced by the action of phenoloxidase on L-3,4-dihydroxyphenylalanine (DOPA) may non-enzymatically polymerize the formation of a black melanin polymer. A prophenoloxidase cascade system may be obtained from silkworm larvae plasma as described by Ashida in Insect Biochem. 11, 57-65 (1981) or U.S. Pat. No. 4,970,152.

The terms "chromogenic phenoloxidase substrate" and "chromogenic substrate" as used herein refer to a substrate of phenoloxidase that generates a colored reaction product. Exemplary chromogenic phenoloxidase substrates are L-3,4-dihydroxyphenylalanine, 3,4-dihydroxyphenethylamine; (dopamine), 3,4-dihydroxyphenyl propionic acid, 3,4-dihydroxyphenyl acetic acid, or catechol.

The term "L-3,4-dihydroxyphenylalanine" or "DOPA" refers to a phenoloxidase substrate. Quinones produced by phenoloxidase action on DOPA or another substrate may be detected as a colored complex with 3-methyl-2-benzothiazolinone hydrazone (MBTH) or derivative thereof. DOPA is also a chromogenic reagent that in turn may be converted into a colored melanin reaction product. The black melanin reaction product can be detected visually or spectrophotometrically at an absorbance in a wide range of wavelength. Absorption at 650 nm is typically used for detection of the melanin polymer.

The term "3-methyl-2-benzothiazolinone hydrazone" or "MBTH" refers to a chromogenic reagent that produces stable colored adducts with quinones. This reaction product can be detected visually or spectrophotometrically. Quinone-MBTH complexes are soluble and have an absorption maximum in a range of 450-510 nm depending on the substrate producing the quinone. Quinone-MBTH complexes visually have a red color. Spectrophotometric methods for determining phenoloxidase and tyrosinase activity using MBTH are described in Rodiquez-Lopez et al., Anal. Biochem. 216:205-12 (1994) and Winder, A. J., J. Biochem. Biophys. Methods 28:173-183 (1994).

The term "3-methyl-2-benzothiazolinone hydrazone derivative" or "MBTH derivative" refers to various compounds having the general structure:

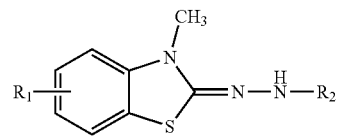

wherein $R_1$ represents H, alkyl, halide, $-NO_2$, $-CO_2$, or $-SO_3$; and;

$R_2$ represents H, or $-SO_2R_3$;

wherein $R_3$ represents alkyl, aryl, and heteroaryl.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

For example, MBTH derivatives include, but are not limited to, the salt of 6-carboxy-3-methylbenzothiazolone hydrazone hydrate (U.S. Pat. No. 5,710,012), the salt of 3-methyl-6-sulfonyl-2-benzothiazolinone hydrazone (U.S. Pat. No. 6,379,915), and the salt of meta[3-methyl 2-benxothiazolinone hydrazone] N-sulfonyl-2-benzensulfonate (U.S. Pat. No. 5,563,031).

3. Detection Assay

Described herein is a sensitive and specific assay for the detection of bacteria in platelet units through measurement of peptidoglycan, a common component of all bacterial cell walls, including Gram-positive and Gram-negative bacteria. Thus, peptidoglycan provides a useful broad-spectrum marker for the presence of microorganisms, such as pathogens, in samples. The assay described herein enables measurement of peptidoglycan either quantitatively or qualitatively, in either the presence or absence of other sample components, such as platelets. In certain embodiments, peptidoglycan may be detected using plasma or hemolymph from invertebrates. In exemplary embodiments, peptidoglycan is detected using plasma or hemolymph from insects. Hemolymph may be isolated using the methods disclosed by Ashida in Insect Biochem. 11, 57-65 (1981), U.S. Pat. No. 4,970,152, 5,585,248, or 5,747,277. Hemolymph may be isolated from insects belonging to the orders including, but not limited to Lepidoptera (such as *Manduca sexta* (tobacco hornworm), *Manduca quinquemaculata* (tomato hornworm), *Gelleria melonella, Hyalphoma ceropia, Bombyx mori* (silkworm)), Diptera (such as *Sarcophaga peregrina* (flesh fly), *Sarcophaga mucosa, Mucsa domestica* (house fly)), Orthoptera (such as *Locusta migratoria, Teleogryllus* (e.g., Emma field cricket), Coleoptera (beetles) (such as *Cerambyx* and *Acalolepa luxuriosa*). Insects may be used at any stage of development and thus may be larvae or adult. In an exemplary embodiment, insect larvae are used. Hemolymph isolated from insects described herein comprises peptidoglycan-binding proteins. In an exemplary embodiment, the assay described herein utilizes a prophenoloxidase cascade system isolated from the hemolymph or plasma of the silkworm larvae, *Bombyx mori*. In an alternate embodiment, β-glucan may be detected using hemolymph or plasma from insects. In an exemplary embodiment, β-glucan may be detected using the hemolymph or plasma of the silkworm larvae, *Bombyx mori*.

Silkworm larvae plasma (SLP) is available commercially from Wako Chemicals, Inc, Richmond, Va. The technology of measuring peptidoglycan or β-glucan in an assay using SLP is covered by U.S. Pat. Nos. 4,970,152, 5,585,248, 5,747,277, 6,034,217, and 6,413,729 issued to Ashida et al., of Japan and is described in Kobayashi et al., FEMS Immunol. Med. Microbio. 28:49-53 (2000). The technologies disclosed in these patents include the description of a reagent comprising a fraction obtained from the plasma of an insect, such as a silkworm, which is capable of specifically reacting with peptidoglycan or β-glucan, and the production of purified recombinant peptidoglycan binding proteins.

By contrast, the technology described herein is considered novel, as the application of the measurement of peptidoglycan or β-glucan to detection of bacterial contamination of samples, such as platelet units, has not yet been disclosed. Further, detecting bacteria in the presence of platelets introduces complexities including inhibition and scattering due to the particulate nature of the platelet suspension. Thus, the methods described by Ashida et al. and Kobayashi et al. cannot be applied to platelets without novel modifications, which we describe herein. This innovation is extremely significant due to the great demand in the blood bank industry for a rapid, sensitive, and specific test for bacteria in platelet units. No such test has been validated and is commercially available at present. Compared to other available methods of detection such as culture, the test described herein is faster and nearly as sensitive and will be an essential tool in the protection of integrity of the blood supply as well as the many thousands of transfusion recipients dependent on sterile platelets each year. Furthermore, the test described herein will enable the extension of platelet unit shelf life beyond the presently enforced five-day limit. The FDA set this limit specifically in response to the risk of bacterial contamination in platelet units, which increases with storage time.

The assay described herein detects peptidoglycan and is thus also distinct from two FDA approved automated platelet culture systems currently available. One conventional system, the Pall BDS, uses changes in oxygen concentration as a result of bacteria growth to provide a practical and reliable test. Since bacteria consume oxygen, abnormally low levels of oxygen in a platelet sample indicate the presence of bacteria. A small volume of platelet concentrate is filtered into a sample pouch, separating bacteria from other cellular elements of the sample. This sample is then incubated with an agent to promote the growth of a wide variety of bacteria species. Oxygen levels are measured and a simple pass or fail reading is obtained (Yomtovian, R. et al. (2001) AABB corporate evening Symposium; October 15). A second currently available system, the BioMerieux BacT/ALERT, automatically detects the presence of bacteria by tracking their production of $CO_2$. A sensor at the bottom of a culture bottle containing the specimen indicates the presence of $CO_2$ by changing color, from gray to yellow (Brecher et al. (2002) Transfusion 42:774-779). Both of these systems require secondary instrumentation for sample analysis and require up to 30 hours for bacterial culture. See Table 1 for method comparison data.

TABLE 1

Comparison of Pall BDS and BacT/ALERT Methods

| | Pall BDS | BacT/ALERT |
|---|---|---|
| Detection Method | $O_2$ Depletion | $CO_2$ Production |
| Negative Predictive Value | | 99.97% |
| Specificity | 100% | 99.8% |

TABLE 1-continued

Comparison of Pall BDS and BacT/ALERT Methods

|  | Pall BDS | BacT/ALERT |
|---|---|---|
| Sensitivity | 95.8-100% | |
| Assay Time | 24-72 hours | 9.2-26 hours |
| Sample Type | Whole blood/apheresis platelets | Apheresis platelets only |

In contrast, the present invention detects peptidoglycan or β-glucan directly. In one embodiment, peptidoglycan is detected on contaminating bacteria. Contaminating bacteria may be Gram-positive and/or Gram-negative bacteria. Non-limiting examples of bacteria that may be detected in contaminated platelet units include *Proteus vulgaris, Yersinia enterocolitica, Serratia marcescens, Enterobacter cloacae, Staphylococcus epidermidis, Staphylococcus aureus, Klebsiella pneumoniae, Bacillus cereus, Escherichia coli, Proteus mirabilis, Pseudomonas aeruginosa*, and *Salmonella cholerae*. Bacteria may represent common skin flora, as listed above, as well as normal and pathogenic gut flora. Examples of pathogenic gut bacteria include, but are not limited to, strains of *Salmonella, Shigella, Campylobacter, Yersina, Vibrio, Caostriduim difficile*, and *Escherichia coli*. Other non-limiting examples of bacteria that may be detected using the assay described herein include a member of the genus *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*.

Bacteria may be detected in the assay protocol as colony forming units (CFU)/ml as low as about 100 CFU/ml, e.g., about 100-200 CFU/ml, about 200-300 CFU/ml, about 300-600 CFU/ml, 600-1000 CFU/ml, about 1000-2500 CFU/ml, 2500-5000 CFU/ml or 5000-10,000 CFU/ml. The CFU/ml of bacteria detected in platelets will depend on the identity of the bacteria and the length of bacterial contamination. In an exemplary embodiment, bacterial species including both Gram-positive and Gram-negative bacteria may be detected at concentrations of approximately 100 CFU/ml, which is similar to the range detected by longer, more conventional culture procedures.

In an alternate embodiment, the detection assay provided herein may be used to detect β-glucan, a cell wall component of fungi, such as yeasts and molds. Yeast and other fungal cells include, but are not limited, to the genus *Acremonium, Alternaria, Amylomyces, Arthoderma, Aspergillus, Aureobasidium, Blastochizomyces, Botrytis, Candida, Cladosporium, Crytococcus, Dictyostelium, Emmonsia, Fusarium, Geomyces, Geotrichum, Issatchenkia, Microsporum, Neurospora, Oidodendro, Paecilomyces, Penicillium, Pilaira, Pityrosporum, Rhizopus, Rhodotorula, Saccharomyces, Stachybotrys, Trichophyton, Trichoporon*, and *Yarrowia*.

Clinical samples that may be tested for bacterial and/or fungal contamination include, but are not limited to blood, blood products, platelet units/collections, platelet concentrates, serum, plasma, other blood fractions, tissue, tissue extracts, urine, lymph, hydration fluid (i.e., IV hydration fluids), dialysis fluid, cerebrospinal fluid (CSF), nutrient fluid, vaccines, anesthetics, pharmacologically active agents, or imagining agents. Wound dressings may also be tested for bacterial and/or fungal contamination. In a further embodiment, a sample may be a suspension or a liquid. Bacteria or fungi present in the sample may be collected and optionally concentrated by centrifugation or filtration. Alternatively, the sample may be dried or evaporated.

In addition, medical devices, agricultural products, environmental products, and manufacturing products, including process samples, may be tested for bacterial and/or fungal contamination using the assay described herein. Non-limiting examples of medical devices that may be tested are catheters, stents, and IVs. Non-limiting examples of agricultural products include food products and the water supply. Testing of the water supply may be extended from water that is consumed by humans and other animals to water that is used in recreational facilities including swimming pools and lakes. Non-limiting examples of environmental products include machinery that is used for processing a wide array of samples and products consumed and used by humans. Non-limiting examples of manufacturing samples include sterile products and their components and intermediates that are manufactured for medical uses.

The detection assay described herein does not require sophisticated instrumentation and presents a rapid and cost-effective approach to screening platelet units for bacterial and fungal contamination. In one embodiment, the colored reaction product may be read visually. In another embodiment, the colored reaction product may be read using a spectrophotometer or an ELISA reader. The detection assay, described herein, provides a positive or negative reading of bacterial or fungal contamination.

The features and benefits of the assay include a sensitivity-detection of common pathogens to less than or equal to about 100 CFU/ml, a specificity of about 100%, a short assay time and the option of immediate readout using visual evaluation. The flexible format and simplicity of the assay lends itself easily to laboratory automation for batch testing in the blood bank or point of use, e.g. testing in the hospital, doctor's office, manufacturing plant, or in the field (depending of course on the sample to be evaluated). Thus, the bacterial detection assay format is simple and straightforward.

In a further embodiment, the assay described herein is an end-point assay. This is in contrast to other assay protocols that are currently available to measure bacterial contamination in samples. For example, one current assay relies on a kinetic assay to measure small changes in transmittance of light during the reaction. This kinetic assay requires the use of special equipment such as a Toxinometer (tube reader) to measure kinetics of changing light transmission. Activation time to measure analyte concentrations in these protocols may range from 20-120 minutes and this procedure in not amendable for testing of multiple samples. The assay method described herein is amendable to testing about 1, 5, 10, 100, 500 or more samples. In certain embodiments, samples can be tested in parallel and stopped at the same time using an inhibitor of phenoloxidase, by adding precipitating acid reagent, or an anionic detergent and measuring the stable and soluble MBTH complexes in the supernatant after a short centrifugation of stopped reaction mixtures. The stopped reaction product is stable for several hours and samples may be read spectrophotometrically in batch. Unlike other assay protocols, which do not include a stop reaction in their protocol, the reaction products generated in the assay described herein can be transferred into non-sterile devices for measurement of the reaction product. Use of non-sterile equipment is more cost efficient and allows the assay to be more transportable to non-clinical settings.

In certain embodiments, the assay described herein may be conducted in less than 1 hour, about 1-2, about 2-3, about 3-4, about 4-5, about 5-6, or about 6-7 hours. In exemplary embodiments, the assay may be conducted in about 1 hour. Assay times over one hour may be required for slow growing bacteria such as *S. epidermidis*.

In an exemplary embodiment, peptidoglycan or β-glucan may be detected in a sample comprising incubating the sample with a prophenoloxidase cascade system, a phenoloxidase substrate that generates a quinone reaction product, and 3-methyl-2-benzothiazolinone hydrazone; and, detecting the formation of a colored prophenoloxidase reaction product, wherein formation of the reaction product indicates the presence of peptidoglycan or β-glucan in the sample. The formation of a colored reaction product further indicates the presence of bacteria or fungi in the sample.

In certain embodiments, the prophenoloxidase cascade system comprises a phenoloxidase activating enzyme, prophenoloxidase, and a serine proteinase cascade. In further embodiments, the prophenoloxidase cascade system may comprise a peptidoglycan binding protein or a β-glucan binding protein. A prophenoloxidase cascade system may be obtained from insect hemolymph or plasma. In an exemplary embodiment, a prophenoloxidase system is obtained from silkworm larvae plasma.

In certain embodiments, a phenoloxidase substrate that generates a quinone reaction product may be L-3,4-dihydroxyphenylalanine, L-3,4-dihydroxyphenolamine (dopamine), 3,4-dihyroxyphenyl propionic acid, 3,4-dihydroxyphenyl acetic acid, or catechol. In an exemplary embodiment, a phenoloxidase substrate that generates a quinone reaction product is L-3,4-dihydroxyphenylalanine (DOPA) or L-3,4-dihydroxyphenolamine (dopamine).

In an exemplary embodiment, one milliliter of platelets are aseptically removed from a sterile platelet unit and centrifuged for five minutes at 14,000 rpm in a standard laboratory microcentrifuge. This assay method is referred to herein as Assay Method 1. The supernatant is removed and the pellet containing platelets and any bacterial contaminants (natural or spiked) are resuspended in approximately 100 μl of extraction solution (0.1 N NaOH). The platelets and any contaminating bacteria are incubated at about 80° C. for about 6 minutes, then approximately 100 μl of neutralization buffer (80 mM MES/10 mM MBTH) is added. The entire sample (approximately 200 μl) of extracted and neutralized platelets is assayed per reaction tube, containing silkworm larvae plasma (SLP) with substrate, as supplied by the vendor (Wako). In an alternate embodiment, the extracted and neutralized platelets may be added to a reaction tube containing reconstituted prophenoloxidase cascade system and MBTH. In a further embodiment, the extracted and neutralized platelets may be added to a reaction tube containing MBTH or a derivative thereof that has been co-lyophilized with a prophenoloxidase cascade system and a phenoloxidase substrate that generates a quinone reaction product. After a one-hour incubation at 37° C., the reactions are stopped with the addition of 100 μl of 10 mM 1-phenyl-2-thiourea. The samples may be measured for a visual color change. An orange or red tube indicates the presence of bacteria. Absence of any color or a yellow tube is negative indicating that no bacteria are present in the sample. In certain embodiments, the reaction tube contents may be transferred to a standard 96 well microplate and the absorbance of each microplate well read spectrophotometrically at about 490 nm in a standard microplate reader, corrected by subtraction of background read at about 650 nm. The absorbance at about 490 nm, corrected by subtraction of background read at about 650 nm, is proportional to the peptidoglycan concentration in the sample.

In an alternative embodiment, the SLP reaction may be stopped by adding an equal volume of 10% trichloroacetic acid (TCA) and centrifuging the sample for 2 to 3 minutes in a table-top centrifuge. Clear supernatant containing MBTH/quinone complexes may be read spectrophotometrically at 450 nm, since the absorbance maximum for MBTH/quinone complexes shifts slightly towards lower wavelengths in acidic conditions.

In certain embodiments, purified, partially digested peptidoglycan may be used as a standard. Further, a standard curve of peptidoglycan may be constructed by serially diluting purified peptidoglycan from about 10 ng to about 150 pg/ml in extracted and neutralized platelets. Approximately 200 μl of each dilution in extracted and neutralized platelets is incubated with SLP or a reconstituted PCS and incubated at 37° C. for one hour.

Peptidoglycan, either in a platelet/bacterial sample or as a standard, may be detected in the assay at concentrations as low as about 0.156 ng/ml, and may range from about 0.100-0.200 ng/ml, 0.200-0.500 ng/ml, 0.500-1 ng/ml, 1-2.5 ng/ml, 2.5-5 ng/ml, 5-10 ng/ml, and 10-100 ng/ml. The concentration of peptidoglycan will be proportional to an absorbance reading at about 490 nm, corrected by the subtraction of background, read at 650 nm.

In exemplary embodiments, the colorimetric reaction is based on a coupling reaction between o-quinones produced from phenoloxidase o-diphenoloic substrates during the enzyme reaction and 3-methy-2-benzothiazolone hydrazone (MBTH). The MBTH-quinone complex is chromogenic and yields a bright red-colored reaction product that may be measured visually or spectrophotometrically. The reaction product has an absorbance maximum in the range of about 470-510 nm and a high molar absorbance coefficient in the range of 27,500-32,500 $M^{-1}$ $cm^{-1}$. Further, the products that are produced in the colorimetric reaction of MBTH with o-quinones are soluble and stable in acidic pH. Thus, the reaction may be stopped with acid and centrifuged to remove aggregated material without significant loss of absorbing material in the supernatant. The cleared supernatant may be measured conveniently using photometric readers, such as spectrophotometers and ELISA readers or by simple visual examination. MBTH adducts in acidic conditions have slightly higher molar absorbency. Replacement of detection methods based on measuring melanin formation in a colorimetric reaction with a MBTH adduct has resulted in a 7 to 10 fold increase in the analytical sensitivity for detection of phenoloxidase activity. Further, by using a reference filter at 650 nm in combination with an analytical filter between 450 and 510 nm, an additional correction for low level residual light scattering can be made.

In exemplary embodiments, the assay method described above utilizes a centrifugation step and subsequent extraction step to separate platelets and any contaminating bacteria from plasma containing inhibitory components that may interfere with the SLP test. The extraction procedure destroys the activity of inhibitory components of plasma and simultaneously solubilizes platelets and bacterial cells, thus reducing the turbidity of the solution. Reduction of turbidity in the solution increases the accuracy of the sample readout. This is a significant improvement over other assay protocols that are currently available. In such protocols, the presence of particles or inhibitory factors in the samples can easily lead to precipitation in the absence of agitation and can alter the measurement by increasing the turbidity leading to a false positive result. Previous attempts by others to eliminate inhibitory factors used extensive dilutions (e.g., 8 to 20 times) that resulted in a decrease in the sensitivity of bacterial detection.

In another embodiment, the assay method described above employs filtration to separate bacteria in a sample from other components in the sample that may interfere with the assay. As exemplified and described below in Example 16, the sample may be filtered through a sterile filter to trap the bacteria present in the sample, the filter rinsed with a solution such as an alkaline solution, and then the filter back-flushed with a rinse solution such as an alkaline solution, thereby eluting the bacteria trapped on the filter. The eluted bacteria may be further processed as described herein to detect the bacteria present in the sample.

In preferred embodiments, the extraction step is an alkaline extraction. In certain embodiments, alkaline extraction may be performed at an elevated temperature. Alkaline extraction, as practiced herein, results in approximately a 10-fold concentration of bacterial contaminants since the platelet/bacteria pellet may be prepared from 1 ml solution of the original platelet preparation, and can be efficiently extracted with 100 µl of sodium hydroxide solution. Further, as desired, a greater or lesser-fold concentration can be achieved. Moreover, alkaline extraction can significantly increase the accessibility of peptidoglycan from bacterial cell wall and can partially hydrolyze peptidoglycan polymer generating fragments, which are more accessible substrates for the prophenoloxidase cascade system. As a result, amplification in the sensitivity of detection of contaminating bacteria in platelet samples may be achieved through the extraction step.

Further, alkaline extraction alters the absorption spectrum of hemoglobin, which can be present as a contaminating factor in some platelet preparations. The alkaline extraction procedure shifts the absorbance of hemoglobin minimizing the overlap in absorbance with the MBTH reaction products.

In exemplary embodiments, alkaline extracted platelets are neutralized with an acid buffering system prior to testing with the SLP reagent. In preferred embodiments, the acid buffering substance is MES containing MBTH reagent in an amount equal to the volume of sodium hydroxide solution used for extraction. A stable lyophilized form of MES/MBTH, which can be reconstituted in water on the day of testing, has been developed. Neutralization of the extracted platelets may be performed to optimize the pH and MBTH concentration for the SLP detection step. Neutralization may be performed with as little as a two-fold dilution of the concentrated platelet extract. The final concentration of platelets in an extracted and neutralized sample is five times that in the original platelet sample preparation. For example, in a typical assay, an aliquot of extracted and neutralized platelets (about 100-200 µl) may be added to a tube containing lyophilized SLP reagent and substrate (DOPA or DOPA/dopamine mixture). The reaction may proceed at 37° C. for a sufficient period of time to observe a color change (e.g., 60 minutes or less) and then may be stopped with an acid reagent (e.g., tricholoracetic acid (TCA), perchloric acid, or tungstocilicic acid) followed by a 2 to 3 minute centrifugation step in a table top centrifuge or by adding a specific potent inhibitor of phenoloxidase (e.g., phenylthiourea (PTU)) before measuring absorbency. The supernatant after centrifugation of the acid-stopped reaction mixture or PTU-stopped reaction mixture may be transferred into regular immunological plates or tubes/cuvettes for spectrophotometric readings at 490 nm. Alternatively, the samples may be read using a two filter approach at 490 nm and 650 nm, as described above. Further, simple visual measurements may be made since a difference in color is used to determine a positive or negative result. In both the acid stopped and PTU-stopped approaches, the sample color is stable for at least several hours when DOPA is used as a substrate.

In other embodiments, platelets and any contaminating bacteria may be extracted using alternate approaches. Alternate extraction approaches include, but are not limited to, enzymatic extraction.

In an alternate embodiment, the binding of a peptidoglycan-binding protein to peptidoglycan may be leveraged though an enzymatic method, as binding triggers a prophenoloxidase enzymatic cascade in the assay system, which utilizes L-3,4-dihydroxyhenylalanine (DOPA) as a phenoloxidase substrate, which in turn may be measured as a colored melanin end product. The colored melanin product is chromogenic and may be measured by visual inspection or through an optical readout.

In certain embodiments, the pelleted platelets and any bacterial contaminants (natural or spiked) may be collected by dilution with water and centrifugation. Pelleted platelets may be resuspended in water for testing in a silkworm larvae plasma (SLP) reaction. This assay method is referred to herein as Assay Method 2. A 100 µl aliquot of the resuspended platelets is assayed per reaction tube containing 200 µl of reconstituted SLP with substrate (as supplied in the Wako SLP kit) in the presence or absence of 100 µl spiked bacteria. After a one hour incubation at 37° C., the sample is divided into two 100 µl aliquots and these are transferred to a standard 96 well ELISA plate and the absorbance of each well is read at 450 or 490 nm in a standard microplate reader. A standard curve of peptidoglycan may be constructed by serially diluting purified peptidoglycan from 500 to 15 pg/ml and treating each dilution as for the samples described above, i.e., 100 µl of each dilution is incubated with 200 µl reconstituted SLP and incubated at 37° C. for one hour. The response of the samples may be interpolated from the peptidoglycan dose response curve, where the absorbance at 490 nm is directly proportional to the peptidoglycan concentration in the sample (FIG. 1).

The foregoing exemplary method may be adapted with no more than routine experimentation for the detection of fungi. In certain embodiments, β-glucan may be detected on the cell wall of fungi. The detection of β-glucan in a platelet sample would indicate that the sample is contaminated with a fungus. In certain embodiments, purified or partially purified β-glucan may serve as a control in the SLP test described herein.

4. Kits

Also provided herein are kits for detecting peptidoglycan or β-glucan in a sample. A kit for detecting peptidoglycan or β-glucan in a sample may comprise a prophenoloxidase cascade system, a phenoloxidase substrate that generates a quinone reaction product, and 3-methyl-2-benzothiazolinone hydrazone or derivative thereof. The prophenoloxidase cascade system is obtained from insect plasma or hemolymph, and in exemplary embodiments, is obtained from silkworm larvae plasma. The prophenoloxidase cascade system used in the kit comprises prophenoloxidase activating enzyme, and a serine proteinase cascade. The prophenoloxidase cascade system may further comprise a peptidoglycan binding protein or a β-glucan binding protein. Still further the kit comprises a phenoloxidase substrate that generates a quinone reaction product. The phenoloxidase substrate that generates a quinone reaction product may be L-3,4-dihydroxyphenylalanine (DOPA), dopamine, or an other mono- or di-phenol compound.

In certain embodiments, a kit for detecting peptidoglycan in a sample may further comprise a peptidoglycan standard, wherein the peptidoglycan standard is isolated bacterial peptidoglycan, whole bacterial extract, or inactivated whole bacteria.

In alternate embodiments, a kit for detecting β-glucan in a sample may further comprise a β-glucan standard, wherein the β-glucan standard is isolated fungal β-glucan, whole fungal extract, or inactivated whole fungi.

In further embodiments, a kit for detecting peptidoglycan or β-glucan in a sample may comprise an extraction solution. The extraction solution may be an alkaline extraction solution. The kit may also comprise a neutralization buffer. Alternatively, the kit may provide 3-methyl-2-benzothizolinone or derivative thereof dissolved in a neutralization buffer. In another alternative, the kit may further comprise a dry detection reagent containing MBTH or derivative thereof co-lyophilized with a prophenoloxidase cascade system and a phenoloxidase substrate that generates a quinone reaction product. The kit may further comprise a stop reagent, wherein the stop reagent is an acid reagent, an inhibitor of phenoloxidase (e.g., phenyl-thiourea), or an detergent.

In further embodiments, a kit for detecting peptidoglycan or β-glucan in a sample may still further comprise instructions for spectrophotometric detection or a color-coded scale for visual evaluation as well as a sterile sample tube for performing the reaction.

Reagents in the kit may be provided in individual containers or as mixtures of two or more reagents in a single container. Any of the reagents may be provided as a liquid or as a dry powder (e.g., lyophilized).

EXEMPLIFICATION

The invention, having been generally described, may be more readily understood by reference to the following examples, which are included merely for purposes of illustration of certain aspects and embodiments of the present invention, and are not intended to limit the invention in any way.

In the examples described below, the platelets that were used in this assay were recovered from 500 ml whole blood donations from single donors or from apheresis and were leukoreduced in the blood bank according to standard procedure. A mix of outdated (older than five days) platelets and fresh, in date, platelet units were used for assay development.

Example 1: Bacteria Spiked Platelets

In order to assess the sensitivity of the assay, spiking studies were performed with the following bacteria species: *Proteus vulgaris, Yersinia enterocolitica, Serratia marcescens* (*S. marcescens*), *Enterobacter cloacae, Staphylococcus epidermidis* (*S. epidermidis*), *Staphylococcus aureus* (*S. aureus*), *Klebsiella pneumoniae, Bacillus cereus, Escherichia coli* (*E. coli*), *Proteus mirabilis, Pseudomonas aeruginosa* (*P. aeruginosa*), and *Salmonella cholerae*. All of these species represent common skin flora. Bacteria species were obtained from the American Type Culture Collection.

Bacteria were cultured and quantified by reconstituting the bacteria according to the vendor's instructions and grown in Trypticase Soy Broth (Becton Dickinson) overnight at 37° C. Bacteria were washed twice by centrifugation in sterile phosphate buffered saline (PBS) and resuspended in 5 ml sterile PBS. Serial 10-fold dilutions were prepared in PBS by adding 100 µl bacterial suspension to 900 µl PBS over 6 dilutions. Multiple Trypticase Soy Agar (TSA; Becton Dickinson) plates were inoculated from dilutions 4 through 6 using a 10 µl sterile inoculating loop, representing dilutions of 1:10,000 through 1:1,000,000. Plates were incubated overnight at 37° C. and the next day visible colonies were counted manually. Colony forming units were calculated by multiplying average colonies counted by the inoculating loop volume and the dilution factor of the bacterial suspension sampled.

In a one series of experiments, using Assay Method 1, a one ml aliquot of spiked platelet suspension was centrifuged for five minutes at 14,000 rpm in a standard laboratory microcentrifuge. The supernatant was removed and the pellet containing platelets and any bacterial contamination was resuspended in 100 µl extraction solution (0.1 N NaOH). The platelets and any contaminating bacteria were incubated at 80° C. for 6 minutes, then 100 µl neutralization buffer (80 mM MES/10 mM MBTH) was added. The entire sample (200 µl) was transferred to a reaction tube containing silkworm larvae plasma (SLP) with substrate, as supplied by the vendor. After a one hour incubation at 37° C., the reactions were stopped by the addition of 100 µl of 10 mM 1-phenyl-2-thiourea and the samples were monitored for a color change visually and spectrophotometrically.

Figure 2:
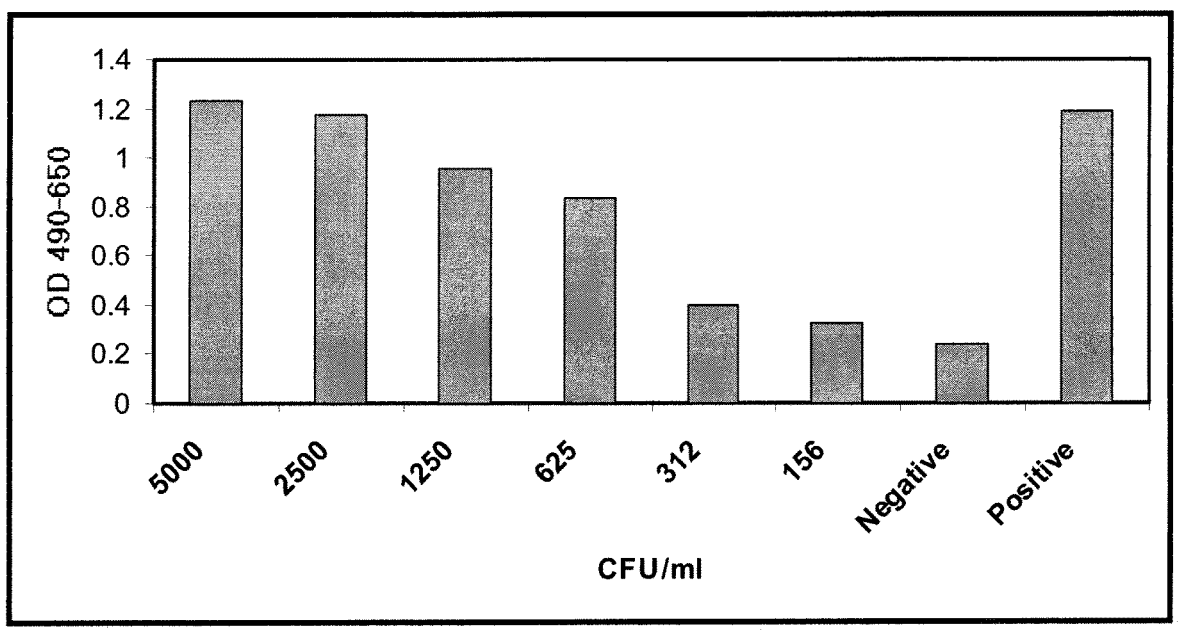
FIG. 2 is a graph showing a dose response curve for detection of S. marcescens spiked into platelets. OD 490-650 refers to a spectrophotometric reading at 490 nm, corrected by subtraction of background, read at 650 nm.

To spike the platelet suspension, serial two-fold dilutions of bacteria were added directly to 1 ml aliquots of platelets such that the final concentration of bacteria in the platelet sampel was between 156 and 5000 CFU/ml, and assayed immediately according Assay Method 1 described above. Platelets were also assayed without added bacteria as a negative control or with the addition of 1 ng/ml purified peptidoglycan as a positive control. The dose response curve of platelets spiked with *Serratia marcescens* is shown in FIG. 2.

Further dose response testing was performed using several bacteria species including *E. coli, P. aeruginosa, S. epidermidis,* and *S. marcescens* or purified peptidoglycan spiked into platelets. Bacteria were spiked into platelets at a 156, 313, 625, 1250, 2500 and 5000 CFU/ml final concentration. Purified peptidoglycan was spiked into platelets at a concentration of 0, 0.156, 0.313, 0.625, 1.25, 2.5, 5 and 10 ng/ml. Assay Method 1 was used and the reaction was monitored both visually in single reaction tubes and spectrophotometrically after the reaction tube contents were transferred to assay plates. OD values at 490 nm, corrected for background read at 650 nm (OD 490-650) provide quantitative results. All bacteria species were detected visually at 156 CFU/ml.

Figure 3:
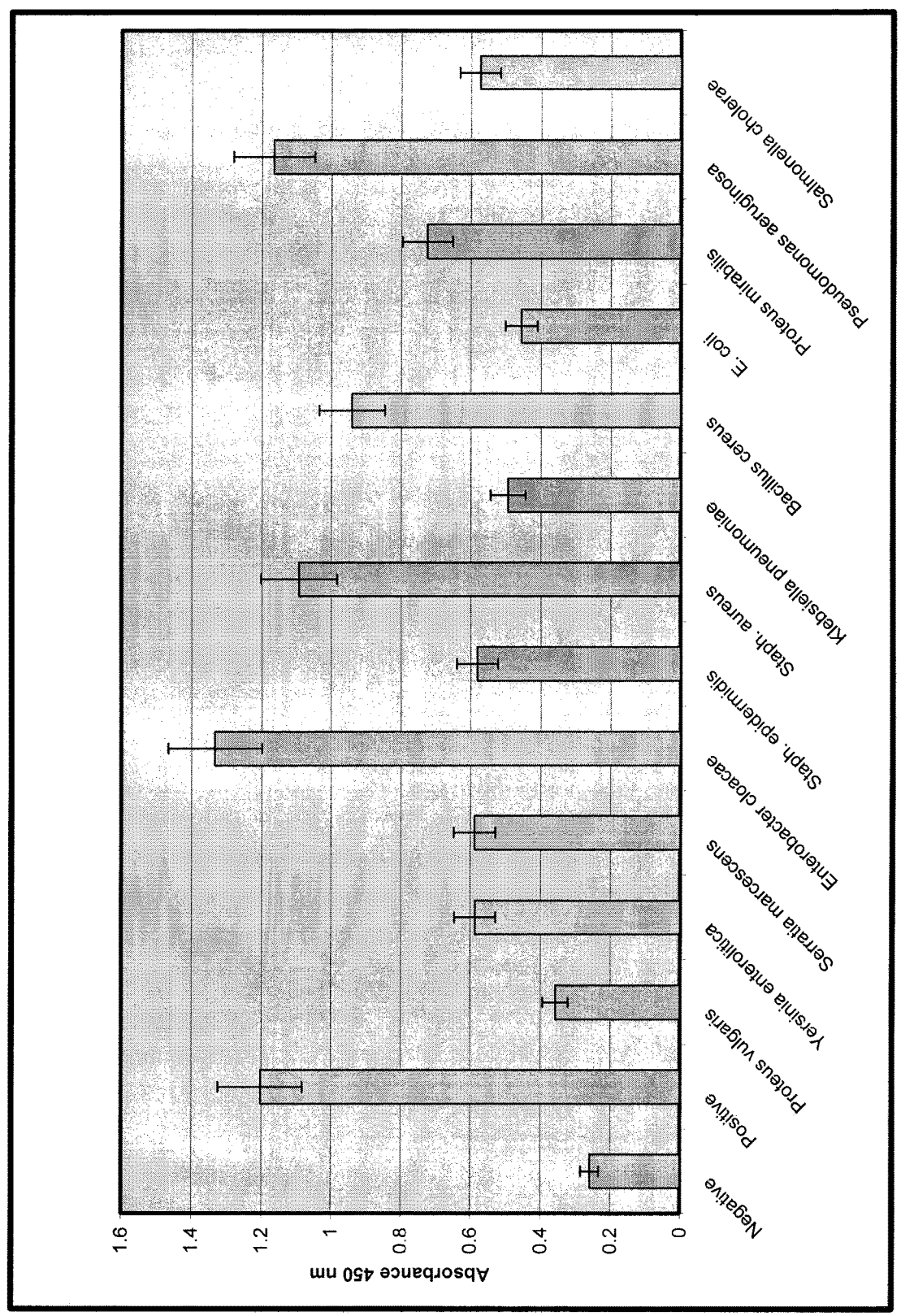
FIG. 3 is a graph showing peptidoglycan in bacteria spiked platelets at an absorbance of 450 nm.

In a second series of experiments, following Assay Method 2, two milliliters of platelets were aseptically removed from a platelet unit and centrifuged for five minutes at 14,000 rpm in a standard laboratory microcentrifuge. The supernatant was removed and the platelets were resuspended in 2 ml sterile deionized water. The platelets were subsequently centrifuged again and resuspended in 1 ml deionized water. 100 µl of platelets were assayed per reaction tube (200 µl of reconstituted silkworm larvae plasma (SLP) with substrate, as supplied by the vendor), in the presence or absence of 100 µl spiked bacteria, at 1000 CFU/ml. After a one hour incubation at 37° C., the sample is divided into two 100 µl aliquots and these are transferred to a standard 96 well ELISA plate and the absorbance of each well is read at 490 nm in a standard microplate reader. In the presence of platelets, all species were detected at 1000 colony forming units (CFU) per ml (FIG. 3).

Figure 4:
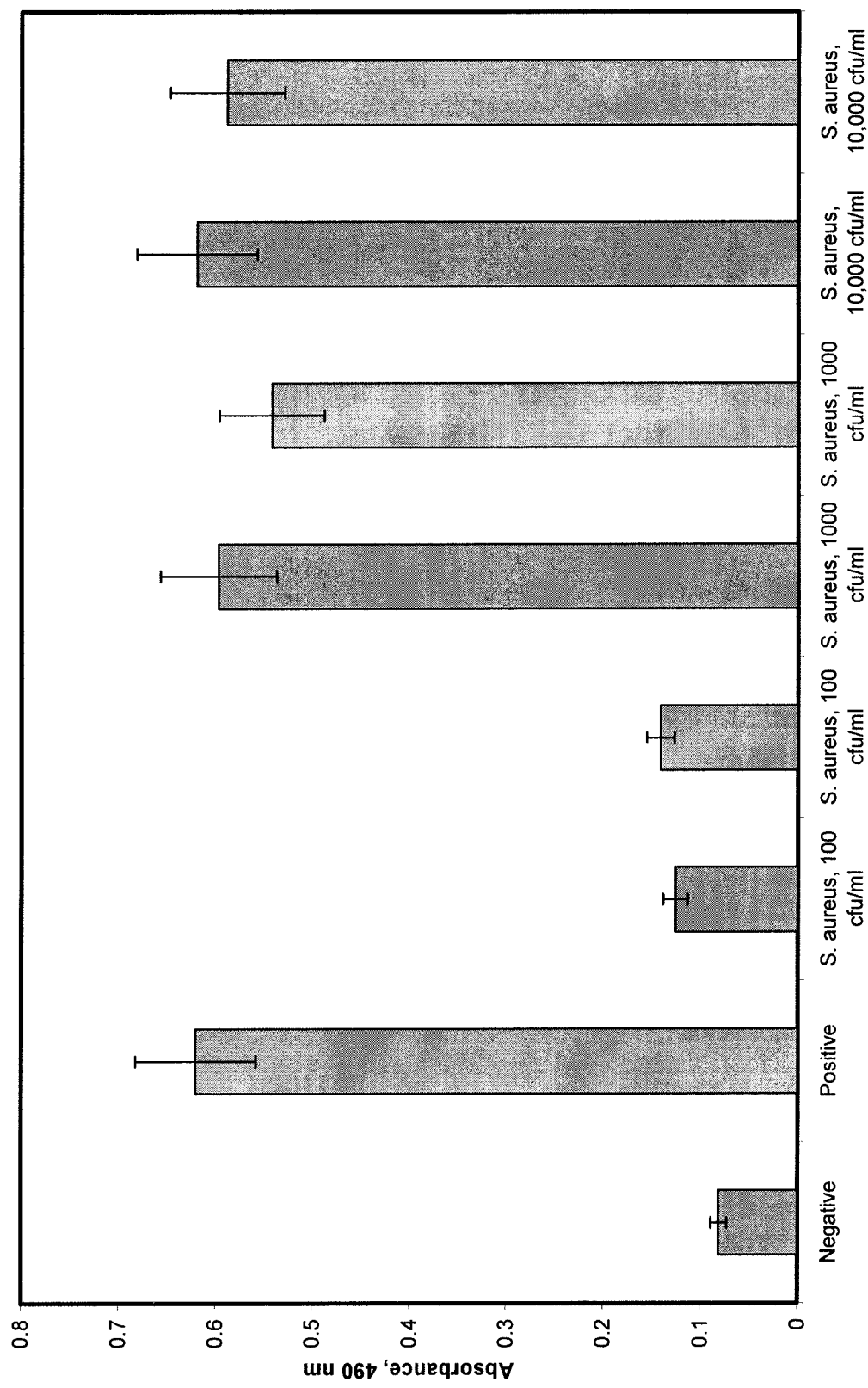
FIG. 4 is a graph showing peptidoglycan in Staphylococcus aureus (S. aureus) spiked platelets at an absorbance of 490 nm.
Figure 5:
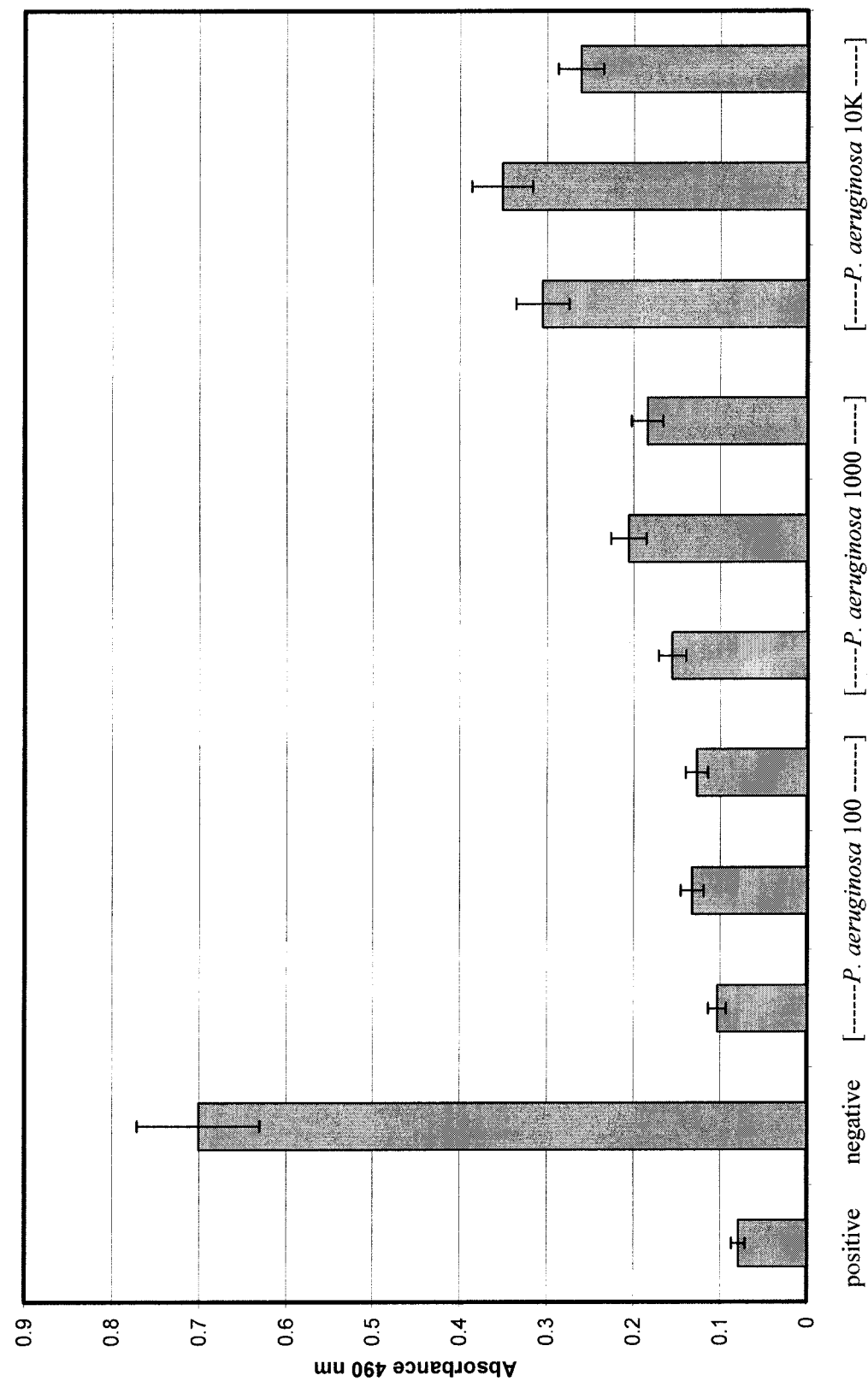
FIG. 5 is a graph showing peptidoglycan in Pseudomonas aeruginosa (P. aeruginosa) spiked platelets at an absorbance of 490 nm.
Figure 6:
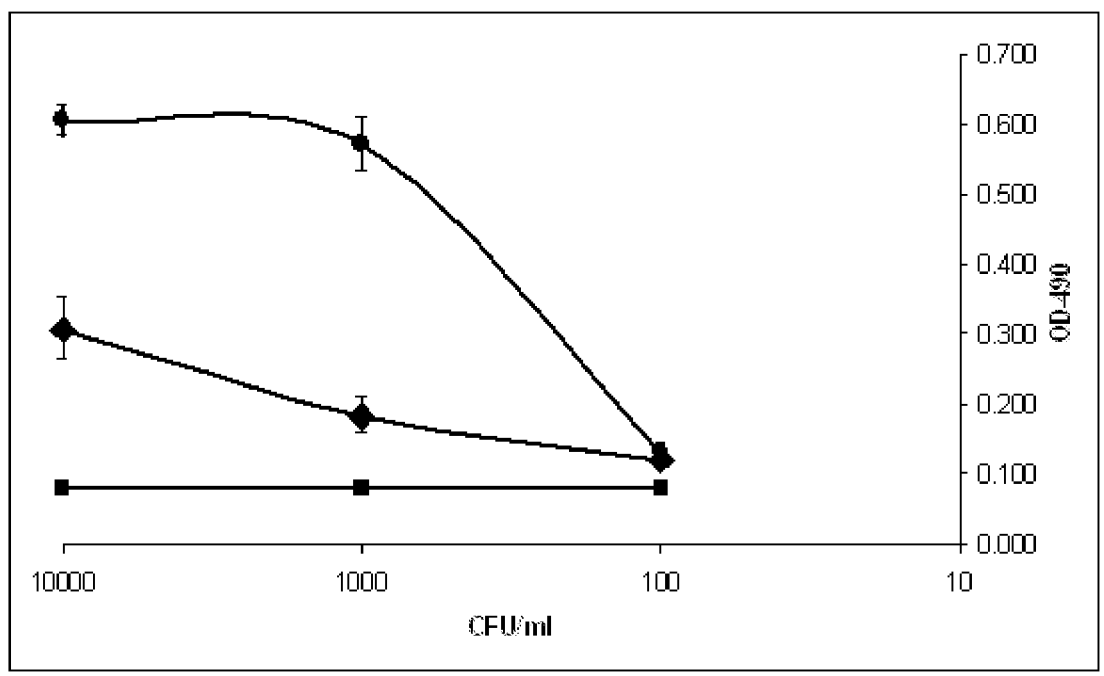
FIG. 6 is a graph showing the detection of bacteria in spiked platelets at an absorbance of 490 nm (■, negative control; ♦, P. aeruginosa spiked platelets; ●, S. aureus spiked platelets).
Figure 7:
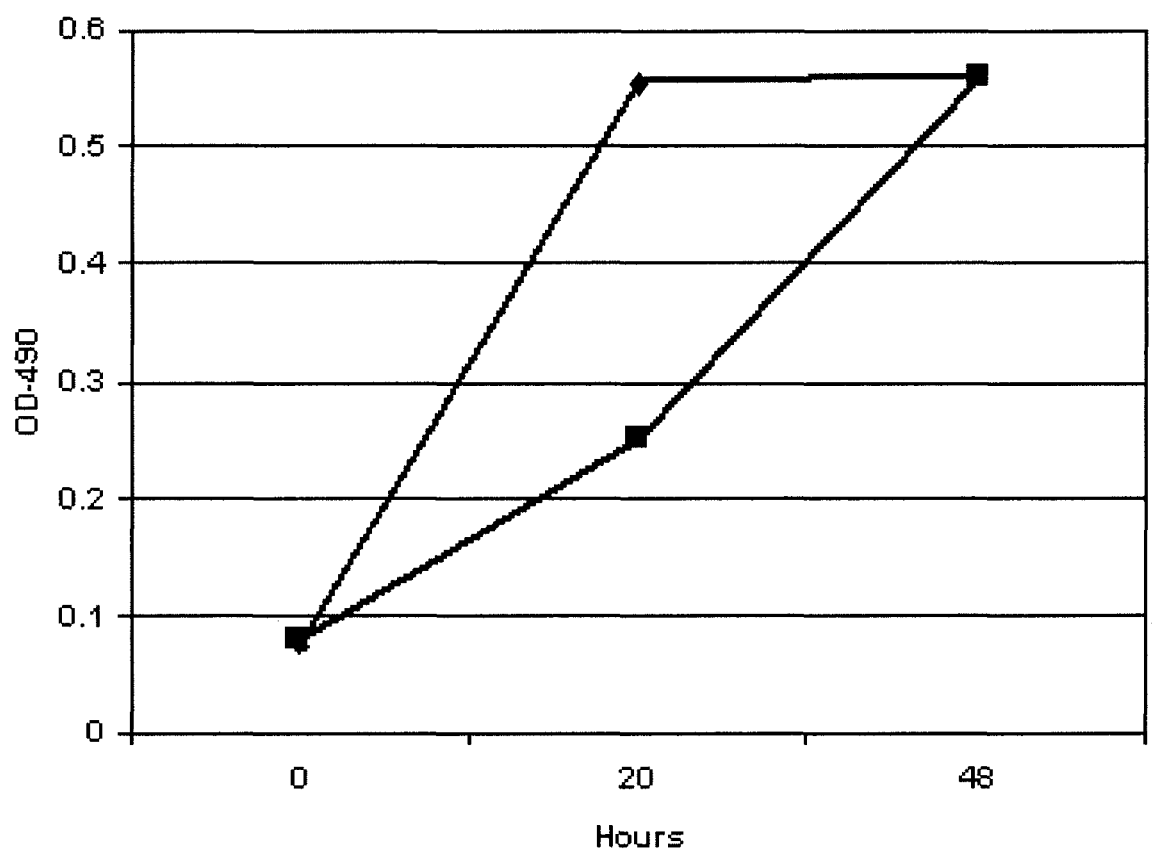
FIG. 7 is a graph showing the detection of bacteria in spiked platelets assayed 20 and 48 hours post-inoculation (■, *S. aureus* spiked platelets; ♦, *P. aeruginosa* spiked platelets; data points are a mean of 4 replicate readings).

*S. aureus* and *P. aeruginosa* were detected at concentrations as low as 100 CFU/ml, under the experimental conditions according to Assay Method 2 (FIGS. 4-6). At concentrations of 100 CFU/ml, 1000 CFU/ml and 10,000 CFU/ml at an absorbance of 490 nm, *S. aureus* and *P. aeruginosa* were detected above the negative control. In FIG. 7, platelet units were spiked with 10 CFU/ml *S. aureus* or at time zero (T=0). Aliquots of 100 µl were assayed as described above at 20 and 48 hours post-inoculation. Data points are a mean of four replicate readings.

Example 2: Time Course Study of Bacterial Growth in Platelets

Figure 8:
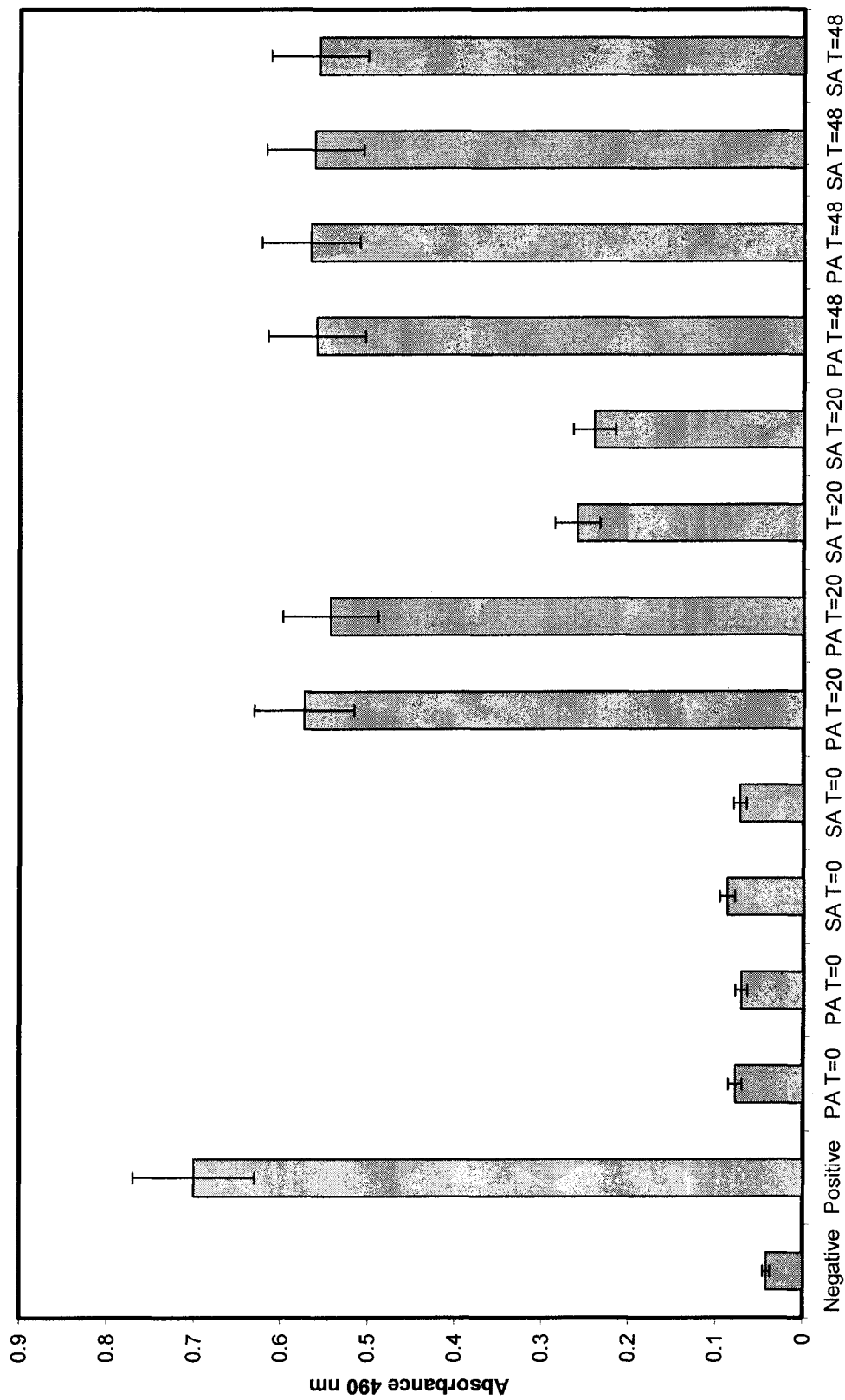
FIG. 8 is a graph showing a time course of peptidoglycan detection in spiked platelets at an absorbance of 490 nm.

In a different approach to assessment of assay sensitivity, a time course study of bacterial growth in platelets was performed using Assay Method 2. In this series of experiments, assay results vs. CFU/ml were determined at increasing times following inoculation of a platelet bag with bacteria. Platelets from two units were removed from platelet bags and placed in sterile 50 ml conical tubes for ease of sampling over time. At time zero, one unit was spiked with 10 CFU/ml of *S. aureus* (indicated as SA in FIG. 8), and the other was spiked at 10 CFU/ml of *P. aeruginosa* (indicated as PA in FIG. 8). Immediately after spiking, one ml samples were taken from each. Following incubation for 20 hours and 48 hours, one ml samples were taken from each. Immediately upon harvest, samples were placed at 4° C. to inhibit further bacterial growth until the time of assay. All samples were processed in parallel as follows: one ml of each was centrifuged at 14,000 rpm in a standard laboratory microcentrifuge. The supernatant was collected and discarded and the platelets were resuspended in one ml of sterile deionized water. After subsequent centrifugation, the platelets were resuspended in one ml of sterile deionized water. Two 100 µl aliquots were assayed per collection point. In less than 24 hours both bacteria species, *S. aureus* and *P. aeruginosa*, were detected in the assay, with good precision. The time point coefficients of variation were generally less than 10% (FIG. 8).

Figure 9:
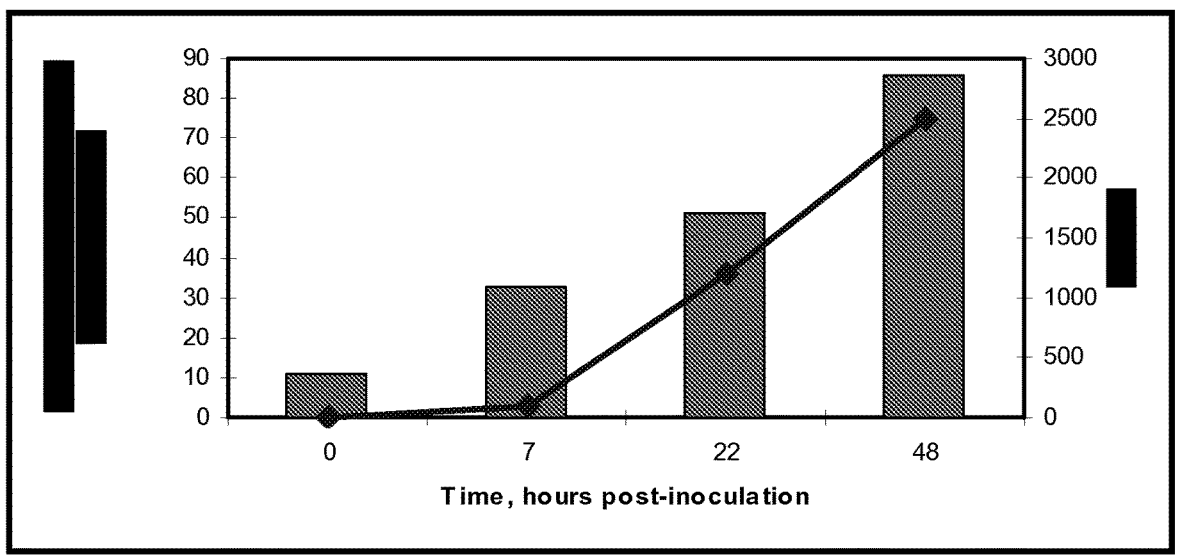
FIG. 9 is a graph showing a time course of detection of *S. epidermidis* spiked at 10 CFU/ml into a platelet bag. OD 490 units normalized to positive control refers to OD 490 units for bacterial samples divided by OD 490 units for a positive control multiplied by 100.

A similar experiment was also performed with *S. epidermidis*. In this experiment, at time zero, platelets were spiked with *S. epidermidis* at 10 CFU/ml. At 0, 7, 22, and 48 hours, one ml samples were removed and stored at 4° C. to inhibit further bacterial growth until the time of assay. Following the last time point, all samples were assayed in parallel. Simultaneously, samples were plated onto TSA plates with a 10 µl sterile inoculating loop. All samples were processed according to Assay Method 1. As shown quantitatively in FIG. 9, growth of *S. epidermidis* can be detected within 7 hours post-inoculation of platelets, at a density of 100 CFU/ml.

Example 3: Specificity of the Assay for Peptidoglycan

Figure 10:
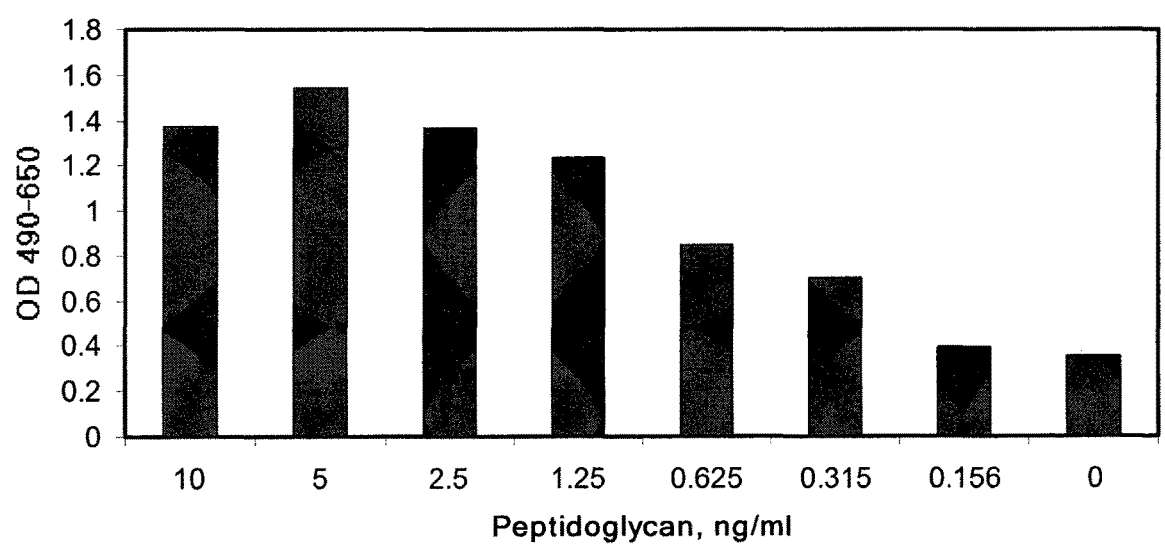
FIG. 10 is a graph showing a dose response curve for peptidoglycan. Purified peptidoglycan was serially diluted into extracted and neutralized platelets. OD 490-650 refers to a spectrophotometric reading at 490 nm, corrected by subtraction of background, read at 650 nm.

In order to demonstrate the specificity of the assay for peptidoglycan, a dose response curve was constructed by serially diluting purified peptidoglycan at concentrations from 10 ng/ml to 150 pg/ml into extracted and neutralized platelets as described in Assay Method 1. The absorbance at 490 nm, corrected for background read at 650 nm, is proportional to the peptidoglycan concentration (FIG. 10). A lower limit of 156 pg/ml peptidoglycan was visually detectable.

Example 4: Extraction Step of the Detection Assay

Figure 11:
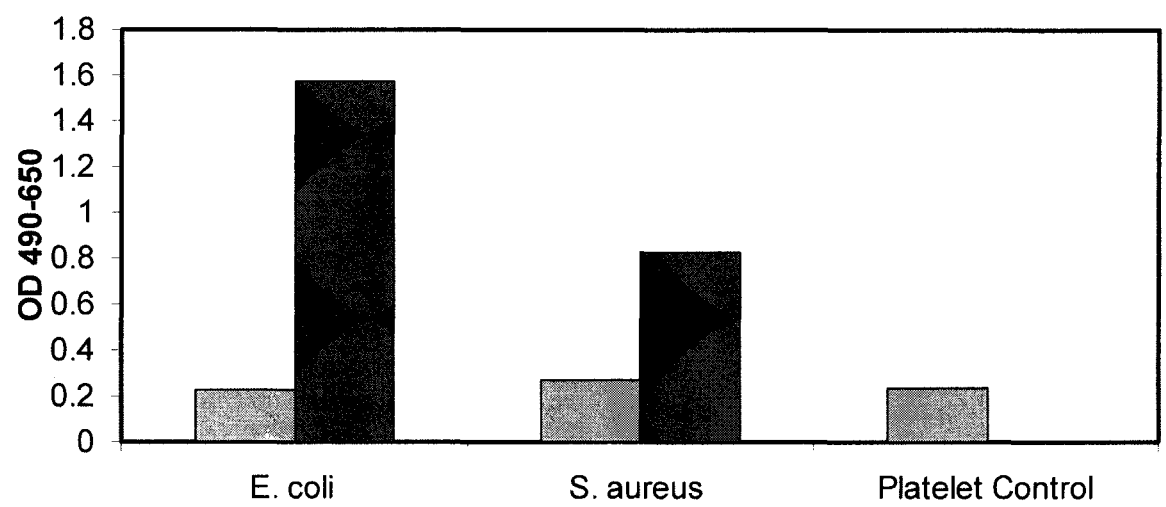
FIG. 11 is a graph showing the enhancement of assay sensitivity by extraction of bacteria (*E. coli* and *S. aureus*) and platelets (▨, no extraction; ▩, with extraction). OD 490-650 refers to a spectrophotometric reading at 490 nm, corrected by subtraction of background, read at 650 nm.

To evaluate the effect of extraction as performed in Assay Method 1, bacteria were added to the platelet sample before or after the extraction step. All samples were assayed as described. The extraction step was found to enhance sensitivity approximately 10-fold for *E. coli* and 2-3 fold for *S. aureus* (FIG. 11).

Example 5: Detection Assay Using Expired Platelet Units

Figure 12:
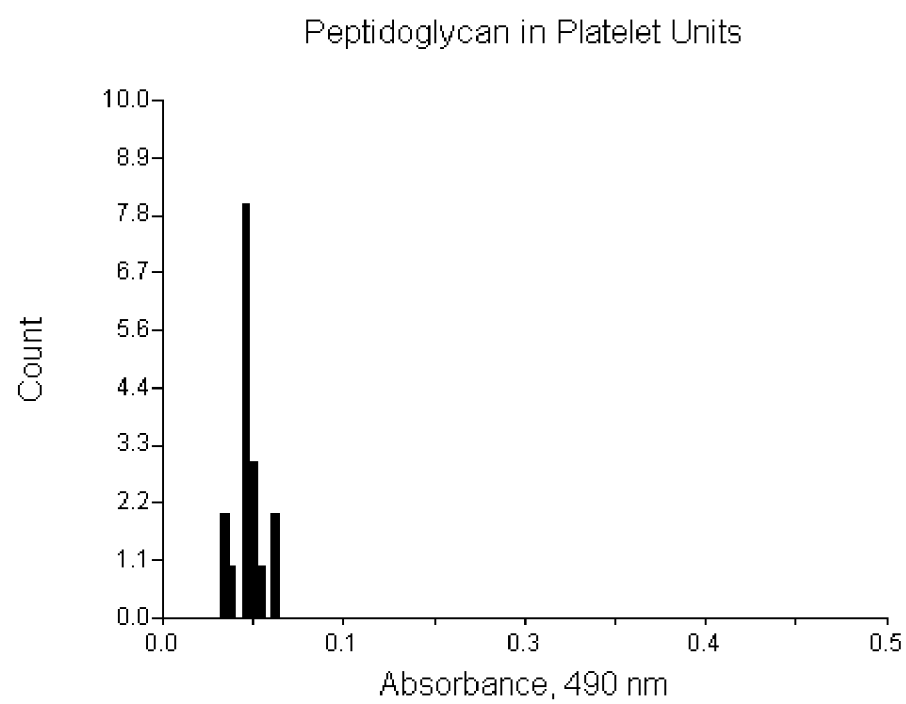
FIG. 12 is a graph monitoring the detection of bacteria in expired platelet units at an absorbance of 490 nm.

In order to assess assay specificity, 17 units of outdated or expired leukoreduced platelet concentrates were processed according to Assay Method 2. Briefly, one ml of each unit was centrifuged, washed with sterile deionized water and resuspended in one ml sterile deionized water. Each one ml aliquot was assayed in 100 µl duplicates in the assay. Each assay reaction was subsequently read in duplicate in a 96 well plate at 490 nm. FIG. 12 is a histogram showing the distribution of optical density (OD) values from 17 platelet donors. The OD values for all 17 donors were very low, indicative of a negative sample, and may be easily discriminated from positive samples with a higher OD value. All units were negative in the assay, with the intra-unit absorbance CVs (coefficient of variation) of less than 5% and the inter-unit absorbance CVs of less than 16%. Intra-unit CV refers to variation between duplicate measurements for each platelet unit and inter-unit CV refers to variation between different platelet units.

Figure 13:
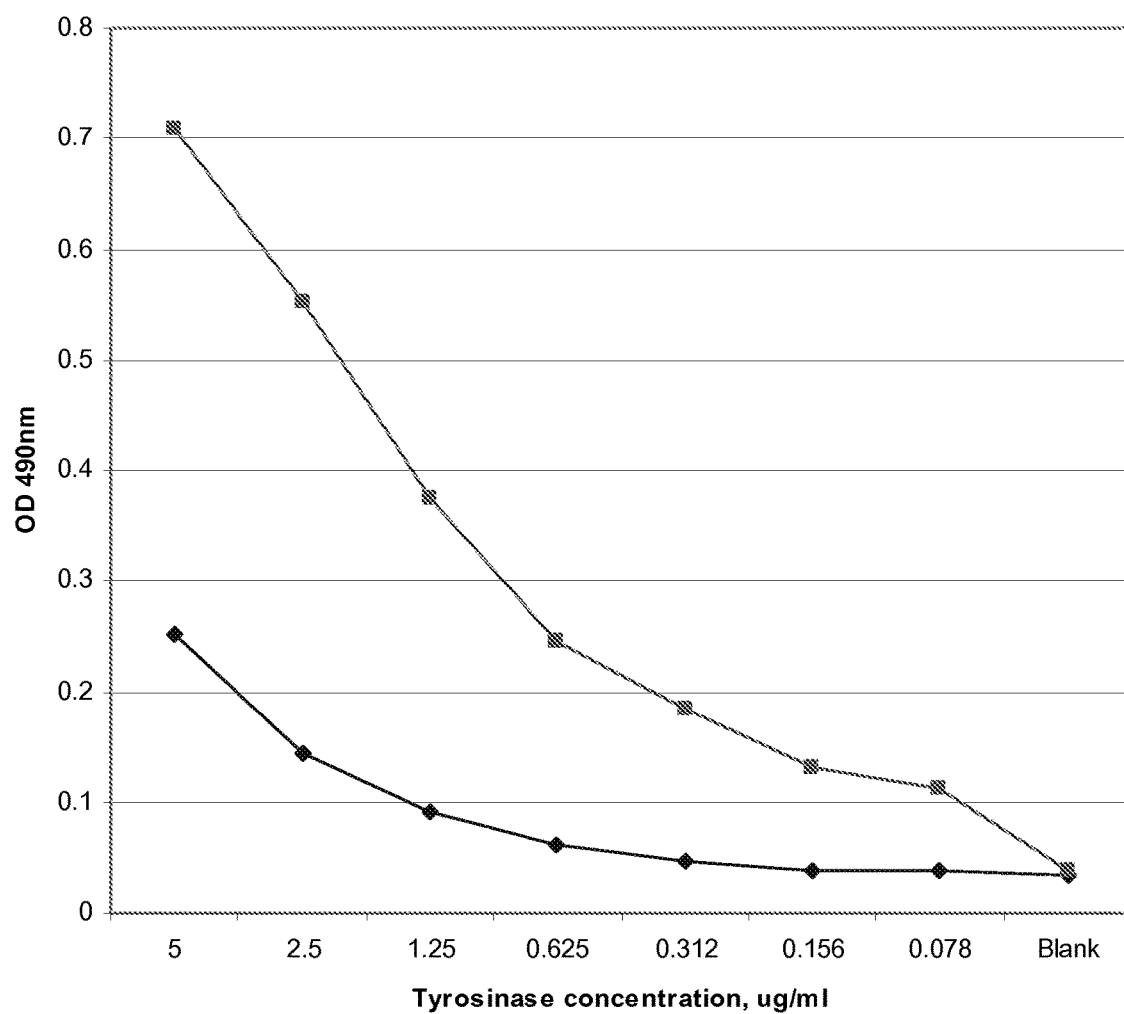
FIG. 13 is a graph showing a comparison of sensitivity for DOPA/melanin and DOPA/MBTH in model experiment with tyrosinase (■, DOPA/MBTH; ♦, DOPA/melanin).

Example 6: Comparison Methods for Detection of Phenoloxidase Activity Based on Melanin Formation and MBTH Procedure A comparison of tyrosinase DOPA/melanin and DOPA/MBTH tests was performed. Mushroom tyrosinase (Sigma) was serially diluted into wells of a microplate containing 0.1M MOPSO buffer, pH 6.5 with a starting concentration of 5 µg/ml and was incubated at 37° C. with 1 mM DOPA or 1 mM DOPA/6 mM MBTH. Reactions were stopped after 25 minutes by adding an equal volume of 10 mM phenylthiourea. Absorbance at 490 nm was measured. Data shown in FIG. 13 demonstrates that approximately an 8-fold lower concentration of tyrosinase in the DOPA/MBTH test provided the same OD values as the DOPA/melanin protocol.

A comparison of DOPA/melanin and DOPA/MBTH SLP tests was also performed. SLP reagent (Wako) containing DOPA was reconstituted in 100 µl diluent (Wako), then added to a 100 µl sample containing peptidoglycan at various concentrations. For testing using the DOPA/melanin protocol, 40 µl 0.1 MOPSO buffer, pH 6.5 was added into all vials. Samples were incubated at 37° C. for 30 minutes and reactions were stopped by adding 50 µl 10 mM PTU. For testing using the DOPA/MBTH protocol, 40 µl 0.1 M MOPSO buffer, pH 6.5 containing 50 mM MBTH was added into all vials and mixtures were incubated at 37° C. for 30 minutes. Reaction was stopped by adding 50 µl 10 mM PTU. All stopped samples were transferred into microplates for reading at 490 nm.

Figure 14A:
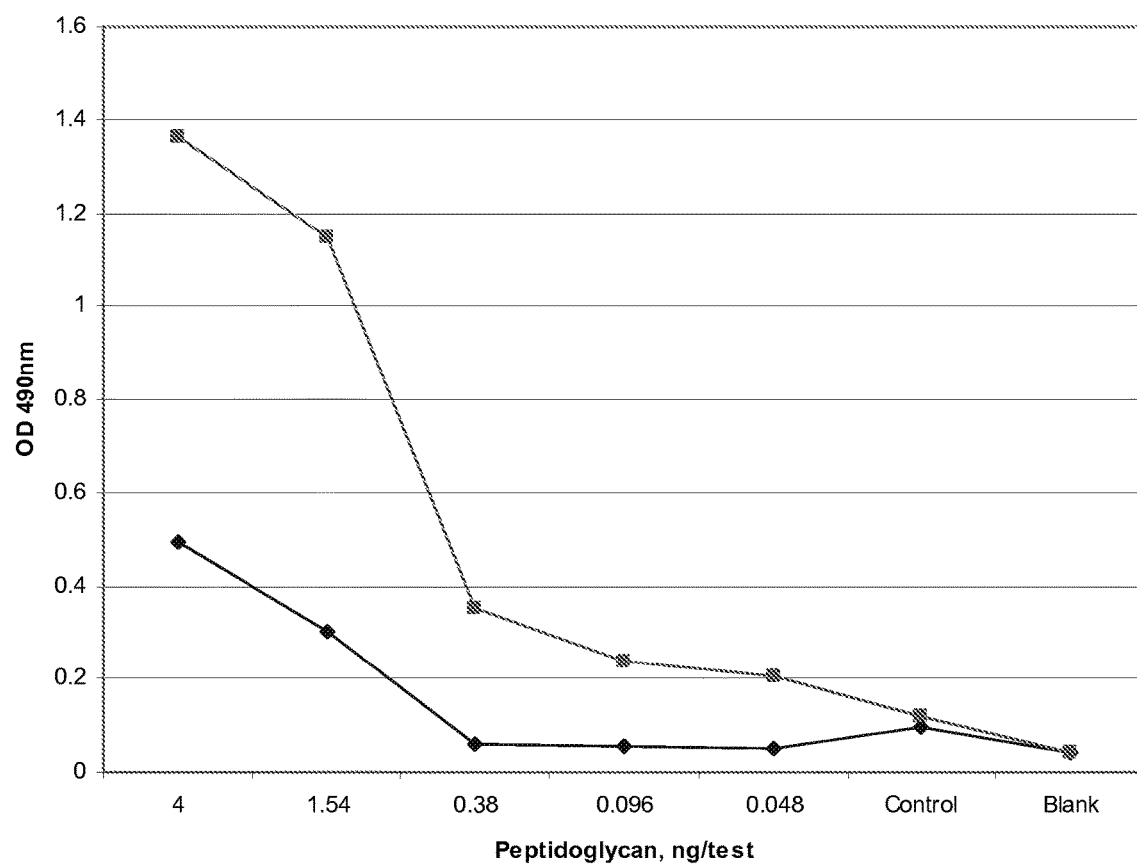
FIGS. 14A and B are graphs showing a comparison of sensitivity for DOPA/melanin, DOPA/MBTH, Dopamine/melanin and Dopamine/MBTH for detection of Peptidoglycan in SLP test (■, DOPA/MBTH; ♦, DOPA/melanin).
Figure 14B:
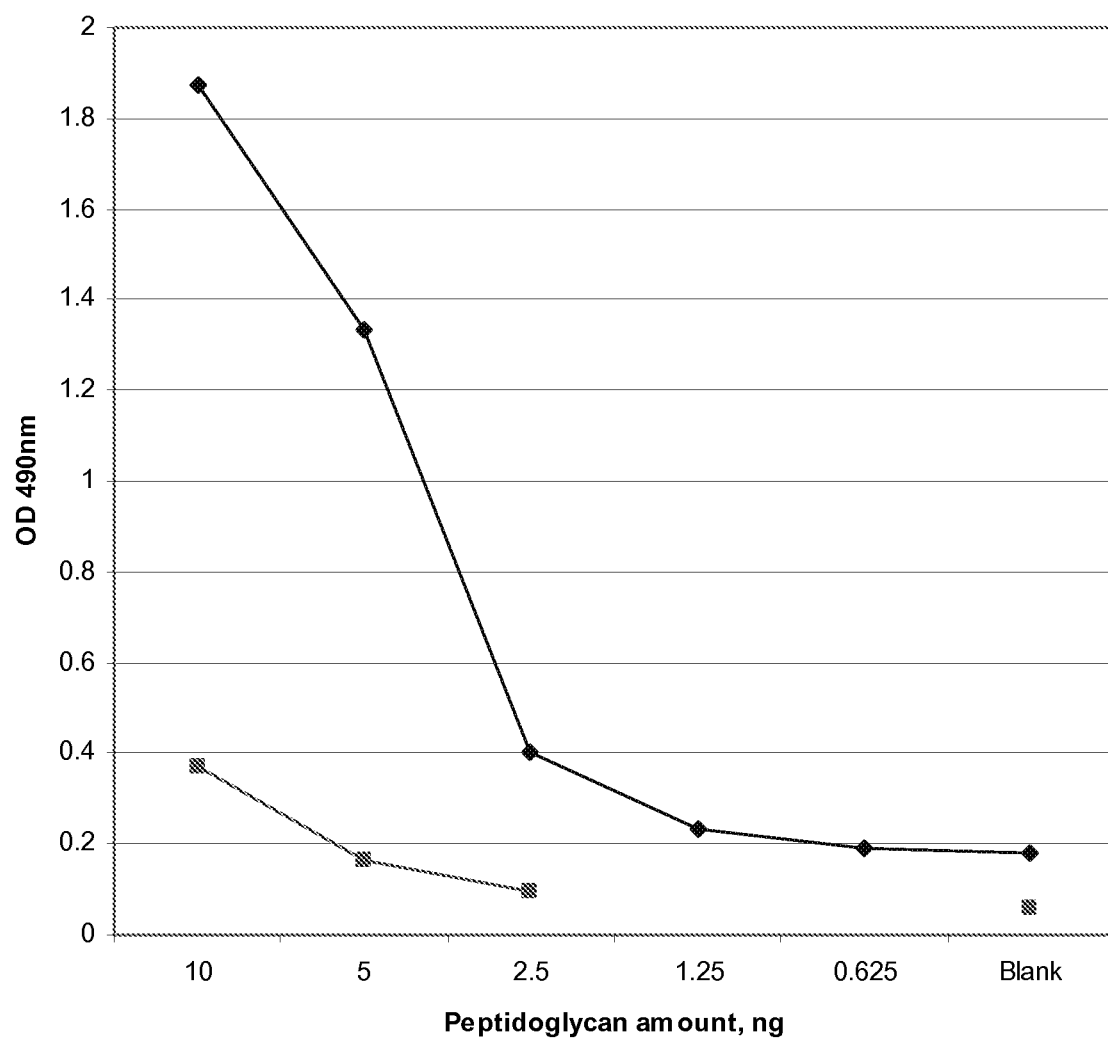

A comparison of dopamine/melanin and dopamine/MBTH tests was also performed. Lyophilized SLP reagent (Wako single reagent) without DOPA substrate was reconstituted into diluent (1.5 ml/vial) and dispensed into sterile tubes (50 µl/tube). PG solutions in diluent and a diluent only control were added (50 µl/tube). 100 µl substrate solution containing 3 mM dopamine or 100 µl dopamine/MBTH solution (3 mM/12 mM) was added to each tube with a subsequent incubation at 37° C. for 30 minutes. Reactions were stopped and absorbency at 490 nm was measured as described above. FIG. 14A shows a significant advantage of the DOPA/MBTH procedure over the DOPA/melanin procedure for detection of spiked peptidoglycan in SLP reagent containing DOPA as a substrate. FIG. 14B shows a significant improvement in sensitivity for detection of peptidoglycan in the SLP test using dopamine as substrate in a dopamine/MBTH protocol.

A comparison of sensitivity for detection of PG spiked into platelets using Melanin and MBTH procedures was also made. Platelets were prepared for testing by diluting platelet preparation 5 times using sterile water with centrifugation for 5 minutes at 14,000 rpm. Platelet pellets were carefully rinsed with water to remove plasma components, and platelets were resuspended in water to the original volume. PG was added into platelet suspension and prepared at various dilutions. Lyophilized SLP reagent (without substrate) was reconstituted in 1.5 ml of diluent. Lyophilized DOPA substrate was reconstituted in 1.5 ml of diluent. Dopamine substrate was prepared at concentration 6 mM in diluent. A mixture of DOPA/Dopamine substrates was prepared by mixing equal volumes of reconstituted DOPA solution and 6 mM Dopamine in diluent.

Reaction mixtures were prepared by adding into sterile tubes 50 µl platelets with PG, 25 µl SLP reagent, and 25 µl substrate solution. For testing using the MBTH protocol, 1.87 µl of 160 mM MBTH in 25% DMFA was added. Tubes were incubated at 37° C. for 60 minutes and the reaction was stopped by adding 50 µl of 10 mM PTU solution. Stopped reaction mixtures were transferred into microplates for reading at 490 nm.

A comparison of sensitivity for detection of bacteria spiked into platelets using Melanin and MBTH protocols was also made. Platelets were prepared using the water washing procedure described above. Platelets were spiked with a small volume of *S. aureus* cells and diluted with platelet suspension to the desired concentration. Single SLP reagents containing DOPA substrate was reconstituted into 100 µl diluent. 1 mM dopamine substrate was prepared in Wako diluent. Reaction mixtures for the DOPA/Melanin test were prepared using a vial with SLP reagent reconstituted in 100 µl diluent, and 100 µl platelet with spiked bacteria or control without bacteria added to the vial. The DOPA/MBTH test was performed similar to the DOPA/Melanin test, but 6.25 µl of 160 mM MBTH solution was also added into the reaction mixture. For the DOPA/Dopamine/MBTH tests, vials with SLP reagents were reconstituted in 100 µl of 1 mM Dopamine. Platelets with bacteria and MBTH were added to the SLP reagents containing Dopamine. All mixtures were incubated at 37° C. for 50 minutes and stopped with 50 µl 10 mM PTU. Absorbance at 490 nm was measured after transfer of stopped reaction products into microwells.

Figure 15:
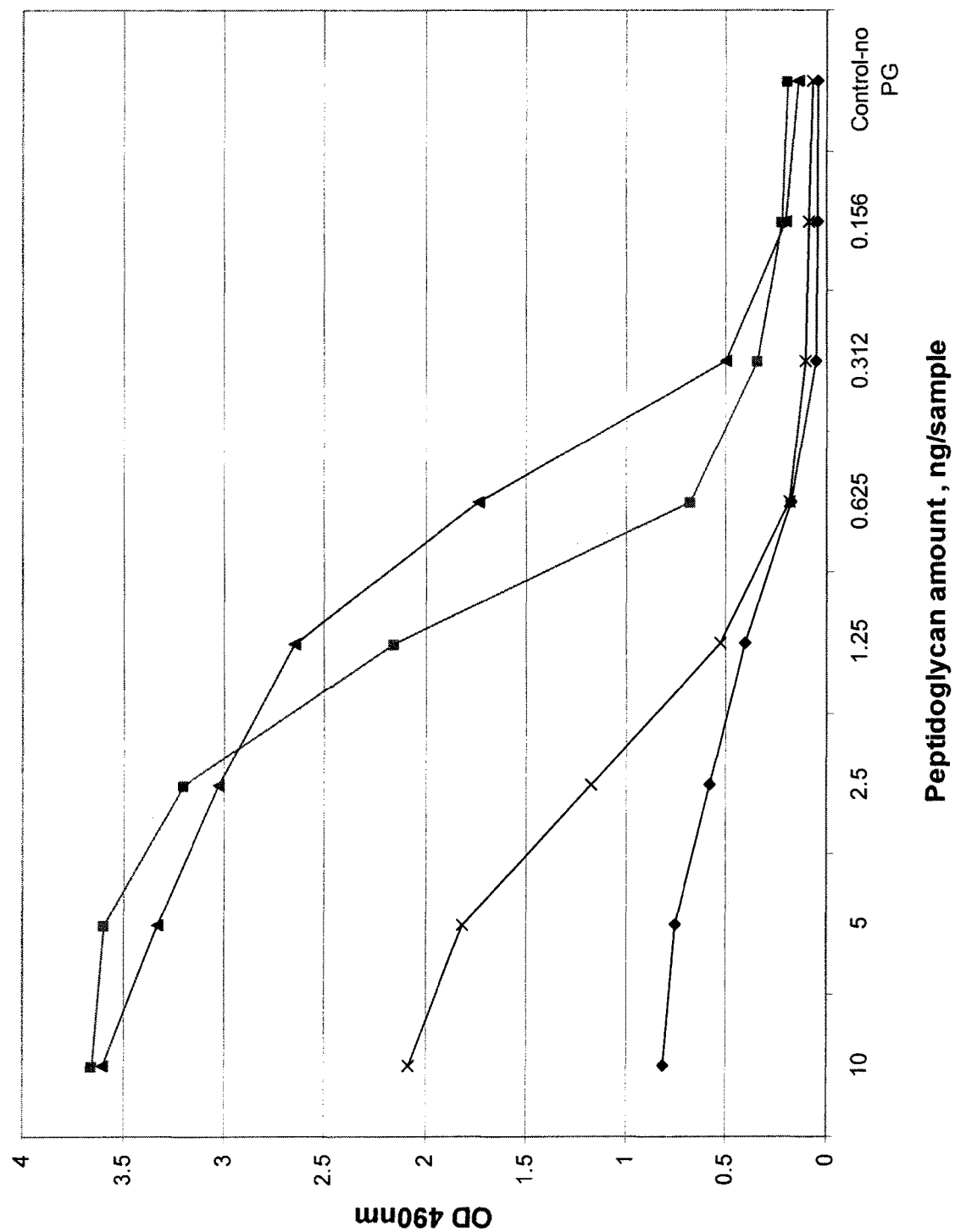
FIG. 15 is a graph showing a comparison of DOPA/melanin and various MBTH substrates (DOPA, Dopamine DOPA/Dopamine mixture) in the MBTH method for detection of Peptidoglycan spiked into the platelet pellet (■, DOPA/MBTH; ♦, DOPA/melanin; ▲, DOPA/Dopamine, MBTH; x, DOPA/MBTH).
Figure 16:
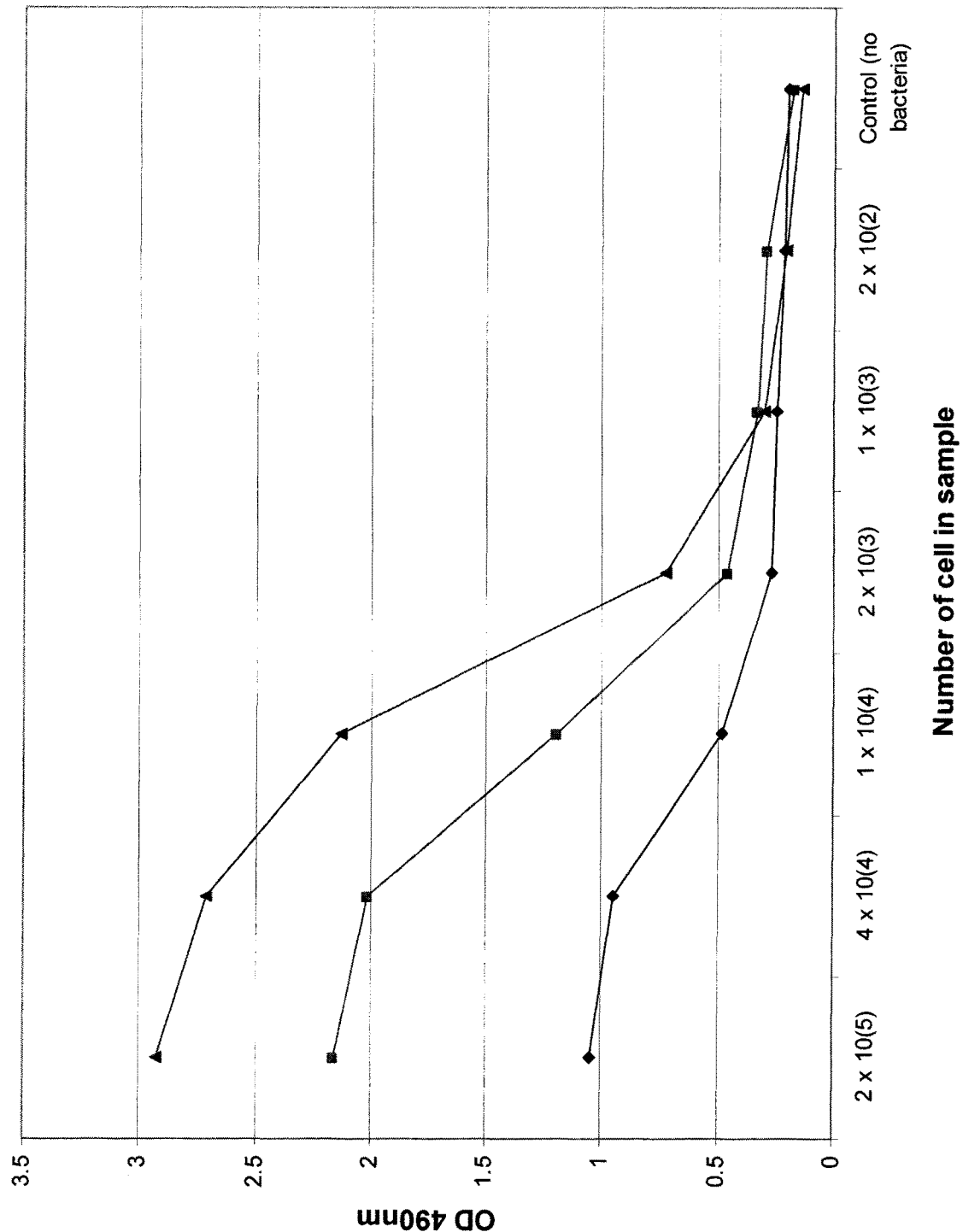
FIG. 16 is a graph showing a comparison of DOPA/melanin and various substrates in MBTH method for detection of bacterial cells spiked into platelet pellet (■, DOPA/Dopamine, MBTH; ♦, Dopachrome; ▲, DOPA/MBTH).

FIG. 15 demonstrates the advantage of the DOPA/MBTH procedure for detection of PG in the presence of platelets. A significant increase in sensitivity is observed when Dopamine or DOPA/Dopamine are used as substrates instead of DOPA. FIG. 16 demonstrates the advantage of the DOPA/MBTH procedure for detection of bacteria spiked into platelets and also shows that the DOPA/Dopamine substrate mixture provides higher sensitivity than DOPA alone.

Figure 17:
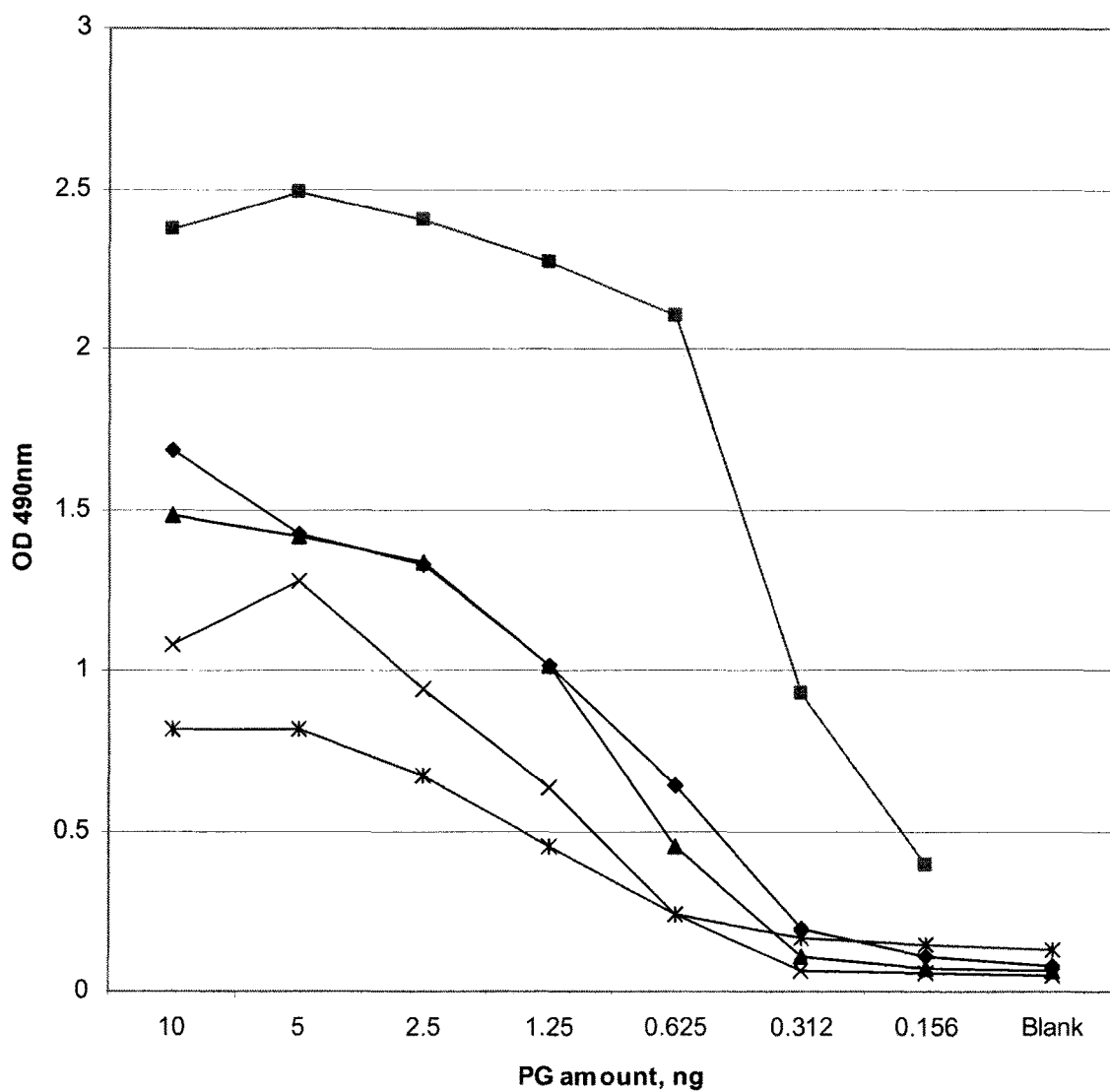
FIG. 17 is a graph showing a comparison of sensitivity for various phenoloxidase substrates for detection of PG in the SLP test.

Example 7: Comparison of Various Phenoloxidase Substrates for Detection of PG Using SLP Reagent and the MBTH Test Lyophilized SLP reagent without substrate was reconstituted in 1.5 ml diluent. PG dilutions were prepared in diluent. Substrate/MBTH mixtures were prepared in diluent at concentration of 3 mM for substrates and 6 mM for MBTH. The following diphenols were used as substrates: DOPA, Dopamine, 3,4-Dihydroxyphenyl acetic acid (DhyAcA), 3,4-Dihydrohyphenyl propionic acid (DhyPrA), and catechol. Reaction mixtures were prepared with 50 µl PG solution, 25 µl substrate/MBTH solution and 25 µl SLP reagent. Incubation at 37° C. for 60 minutes. Reactions were stopped by adding 100 µl 10 mM PTU. FIG. 17 shows that Dopamine is the substrate which provides the highest sensitivity in MBTH test.

Example 8: Determination of Optimal MBTH Concentration in the DOPA/MBTH Test

Figure 18:
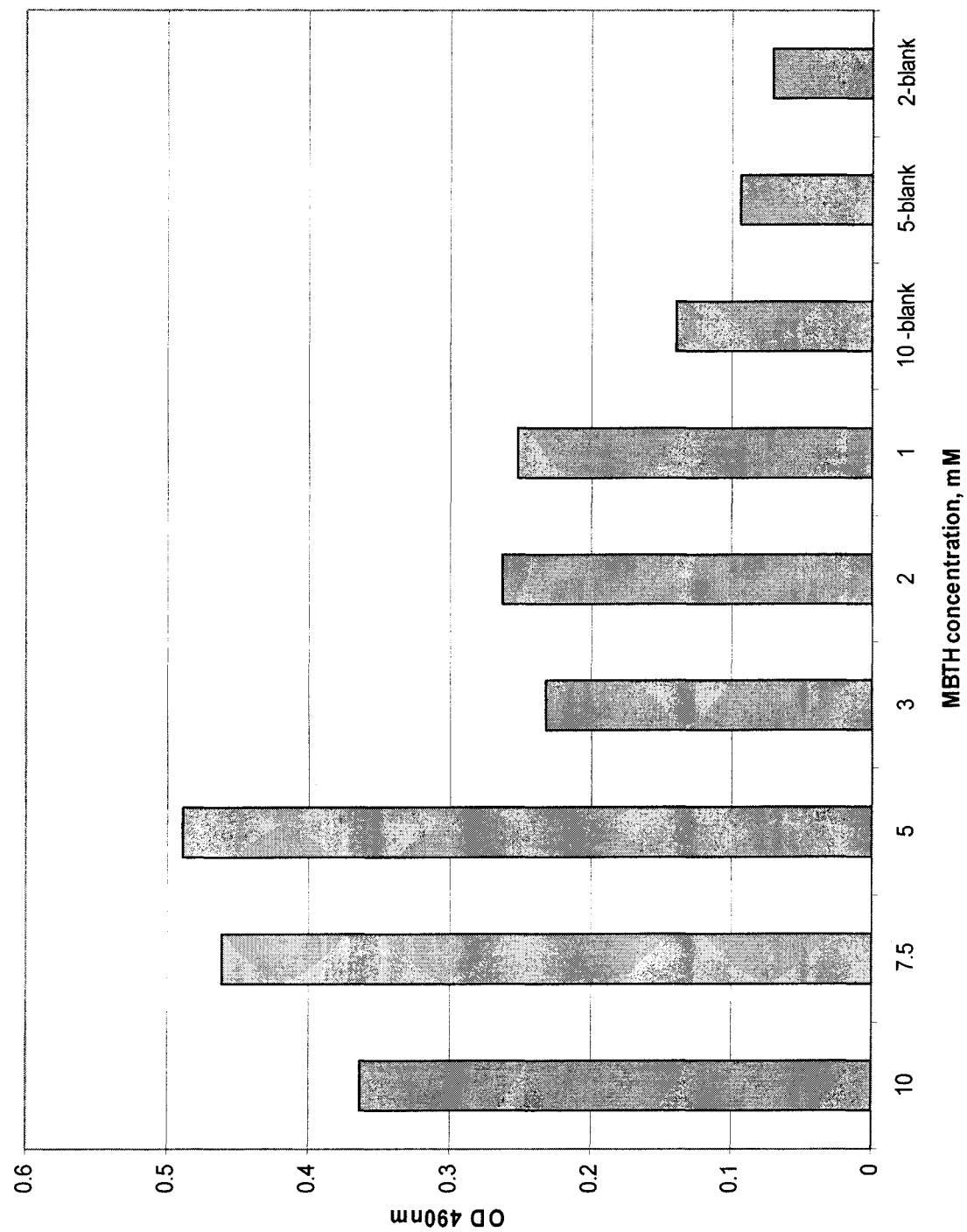
FIG. 18 is a graph showing a determination of optimal concentration for MBTH.

SLP reagent with DOPA was reconstituted in diluent at 100 µl per vial. PG solution (50 µl) containing 10 ng PG was added into sterile tubes. 50 µl SLP reagent was added into each tube, followed by 10 µl MBTH solutions containing 2.5% DMFA (100 mM, 75 mM, 50 mM, 30 mM, 20 mM, and 10 mM). Mixtures were incubated at 37° C. for 30 min and stopped with 10 µl of 10 mM PTU solution. FIG. 18 shows that a concentration of MBTH around 5 mM is optimal for the DOPA substrate used in the WAKO SLP reagent.

Figure 19:
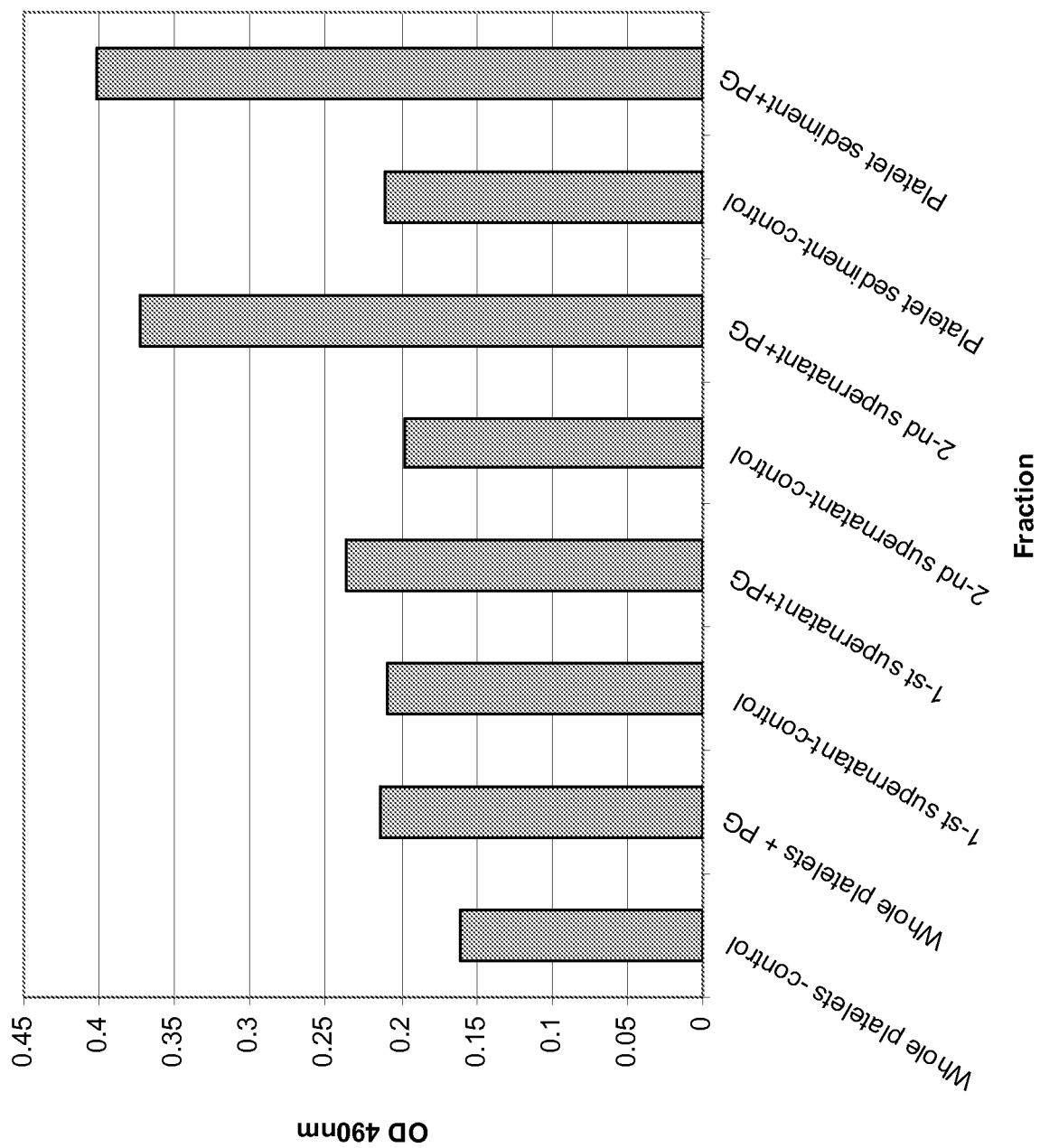
FIG. 19 is a graph showing an analysis of localization of inhibitory activity in platelet preparations. The distribution of inhibitory activity is shown between a platelet pellet and plasma containing supernatant (▨, DOPA/MBTH stopped test).

Example 9: Analysis of the Distribution of Inhibitory Factors Between Platelet Pellet and Plasma Fraction of Platelet Preparation An aliquot of platelet preparation was centrifuged at 14,000 rpm for 5 min, and the supernatant was removed and kept for testing. The platelet pellet was resuspended in volume of diluent equal to the original volume of platelet preparation, and centrifugation was repeated. The second supernatant was likewise separated from the pellet and saved. The pellet was again resuspended in original diluent volume. PG solution was added into portions of each non-fractionated platelet preparation, first supernatant, second supernatant, and resuspended pellet, to concentration 1 ng/ml. 100 µl of each fraction with and without spiked PG was mixed with 100 µl SLP reagent containing DOPA and 5 µl of 100 mM MBTH solution was added into each mixture. Tubes were incubated at 37° C. for 50 minutes and the reaction was stopped with 50 µl of 10 mM PTU. Stopped mixtures were transferred into microwells for reading at 490 nm. FIG. 19 demonstrates that only a small signal is present in non-fractionated platelets with spiked PG and in the first supernatant containing the plasma fraction of platelet preparations. Spiked PG can be easily detected in the second supernatant and the washed platelet pellet, which contains only trace amount of plasma.

Figure 20:
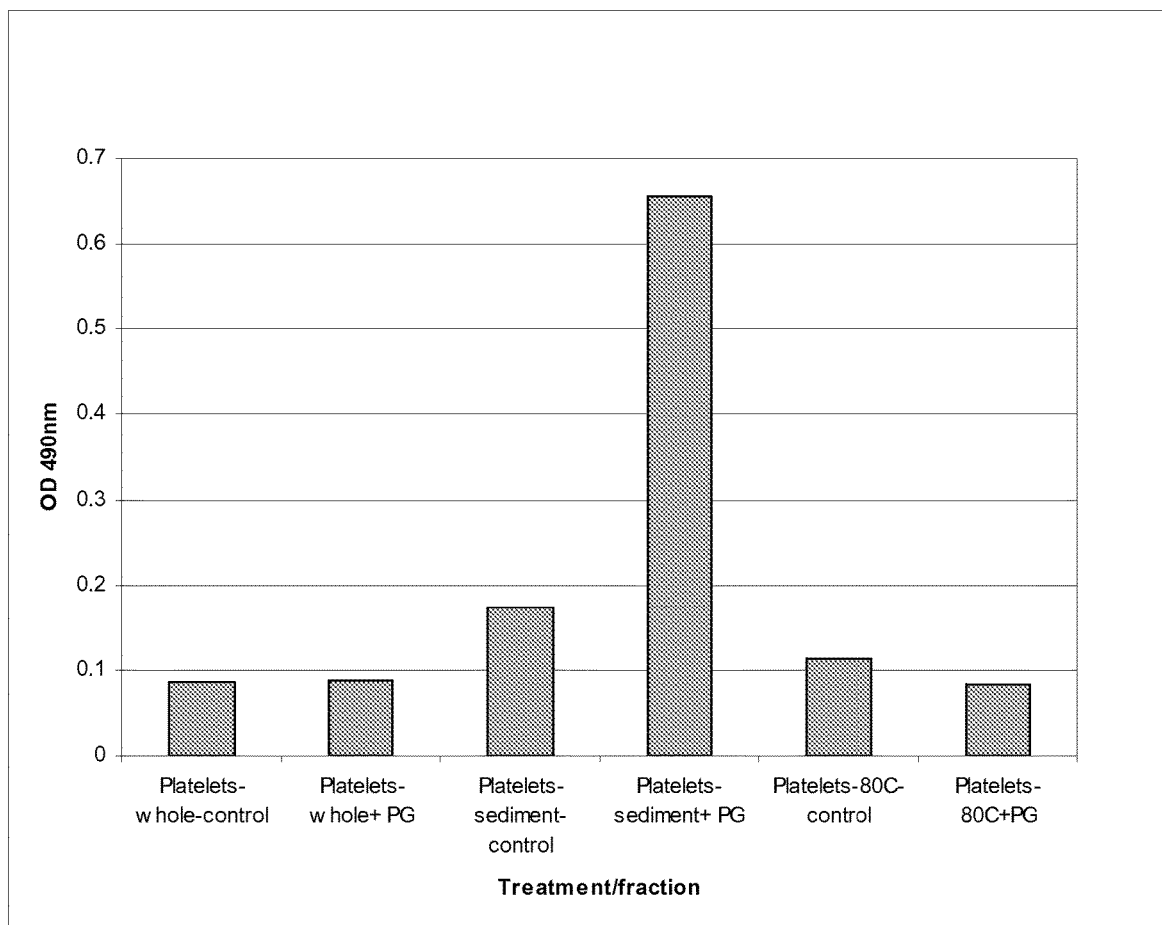
FIG. 20 is a graph showing a demonstration of the inability of simple heat treatment to inactivate inhibitory activity in the platelet preparation.

Example 10: Effect of Short High Temperature Treatment on Activity of Inhibitory Factors in Platelet Preparation One aliquot of platelet preparation was incubated at 80° C. for 5 minutes. A second aliquot was diluted 10 times with water and centrifuged. Platelet pellets were resuspended in original volume of diluent. PG was added into tubes containing whole non-fractionated platelets, heat-treated platelets, and platelet pellets to concentrations of 1 ng/ml. Samples with spiked PG and appropriate control (100 µl) were mixed with 100 µl reconstituted SLP reagent containing DOPA. 10 µl MBTH solution (100 mM in 2.5% DMFA) was added. Reaction mixtures were incubated at 37° C. for 60 minutes and stopped with 50 µl 10 mM PTU. The data presented in FIG. 20 shows that spiked PG can be detected only in the washed platelet pellet. Whole non-fractionated platelets containing plasma with or without short high temperature treatment contain inhibitory activity, which inhibits the reaction of PG with SLP.

Example 11: Effect of Temperature and Time on Efficacy of Alkaline Extraction Procedure for Detection of Bacteria in Diluent

Figure 21:
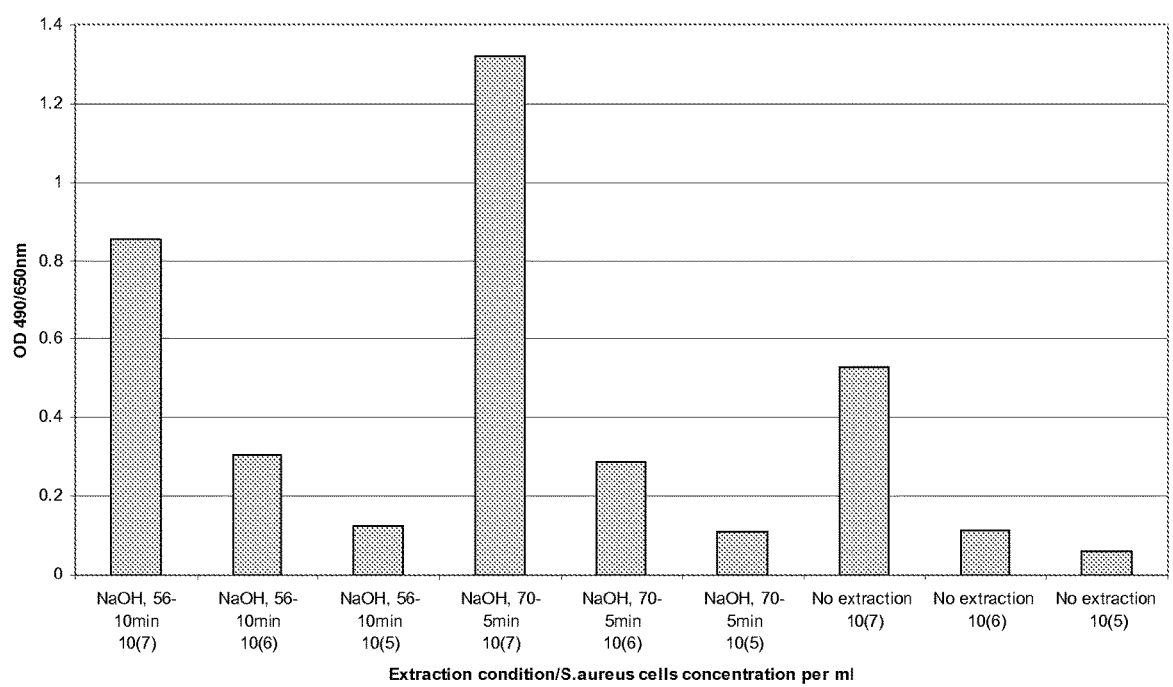
FIG. 21 is a graph showing the effect of alkaline extraction on sensitivity of SLP/MBTH test. *S. aureus* cells were spiked into the diluent supplied with the Wako SLP kit.

*S. aureus* cells were diluted in diluent to a concentration of 10(7), 10(6) and 10(5) cells/ml. 100 µl of each sample was mixed with 100 µl 10.2N sodium hydroxide. As a control, we tested the effect of alkaline extraction and added sodium hydroxide/MES buffer pH 6.8 into a set of tubes with spiked bacteria. Tubes with added sodium hydroxide were incubated at 56° C. for 10 minutes or at 70° C. for 5 minutes. After heat treatment neutralizing solution containing 0.2 M MES was added. The final pH of neutralized samples was between 6.8-7.2. 100 µl neutralized samples and non-treated controls were transferred into tubes containing 100 µl reconstituted SLP reagent with DOPA and incubated at 37° C. for 60 minutes. Reactions were stopped by adding 50 µl 10 mM PTU. FIG. 21 shows that both alkaline extraction procedures performed at 56° C. for 10 minutes and 70° C. for 10 minutes increased sensitivity for detection of bacteria in diluent. Higher temperature (70° C.) provided a significant increase in the sensitivity.

Example 12: Optimization of Alkaline Extraction Procedure for Platelet Pellet

Figure 22:
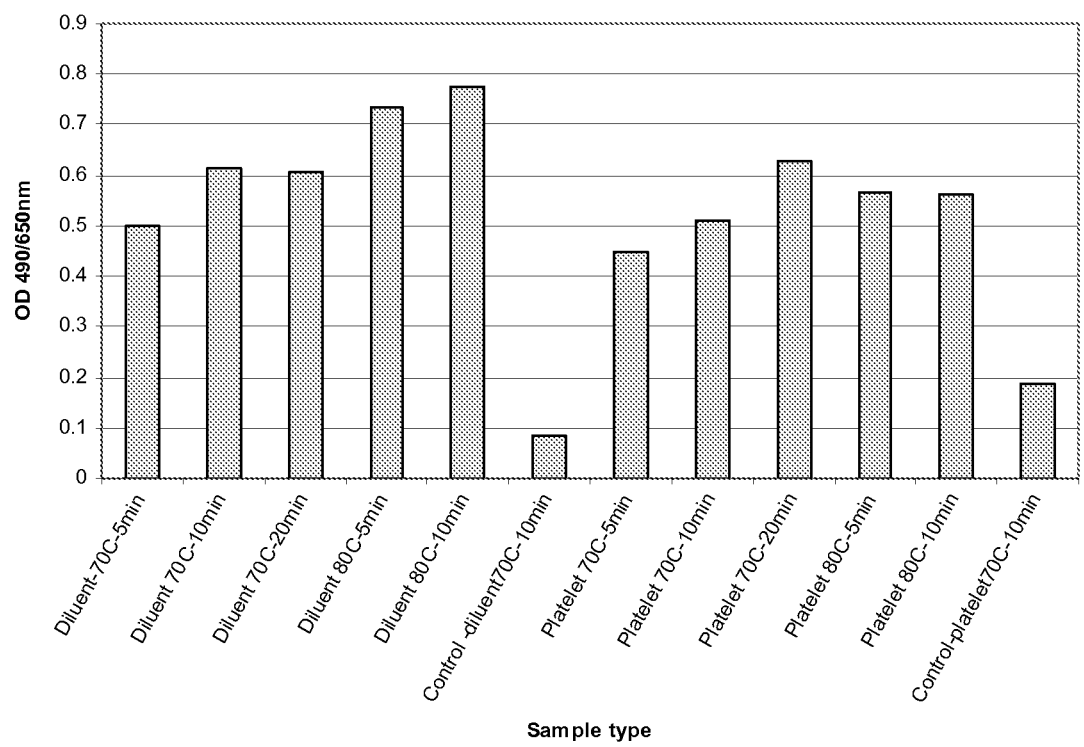
FIG. 22 is a graph showing the effect of extraction temperature and time on the SLP/MBTH test. *S. aureus* cells were spiked into platelets.

*S. aureus* cells were spiked into platelet preparations to concentration 10(6) cells/ml. Platelet pellets were collected from 1 ml original undiluted platelet preparations and platelets with spiked bacteria were collected by centrifugation at 14,000 rpm for 5 minutes. In parallel, *S. aureus* cells were spiked into diluent to the same concentration, 10(6) cells/ml. 100 µl sodium hydroxide solution was added into all tubes containing diluent with cells or platelet pellets. Tubes were incubated at various conditions, 70° C. for 5 minutes, 70° C. for 20 minutes, 80° C. for 5 minutes and 80° C. for 10 minutes. 48 µl 0.2 M MES was added to neutralize extracted samples. 50 µl neutralized samples were transferred into sterile tubes with 50 µl reconstituted SLP reagent containing DOPA. 10 µl 50 mM MBTH solution was added to each tube. Mixtures were incubated at 37° C. for 45 minutes and reactions were stopped with 10 µl 10 mM PTU for reading in microwells. FIG. 22 shows that extraction at higher temperature (80° C.) or for longer periods of time provides increased sensitivity for extraction of bacterial cells in diluent in the absence of platelets as well as for the extraction of bacteria in the presence of large amounts of platelets. The data also demonstrates that presence of concentrated platelet in samples does not dramatically change the sensitivity of the SLP test. The signal was identical for bacteria spiked into platelets, which are 10 times more concentrated than in original platelet preparations, and was only slightly less than signal from the same amount of bacterial cells spiked into diluent.

Figure 23:
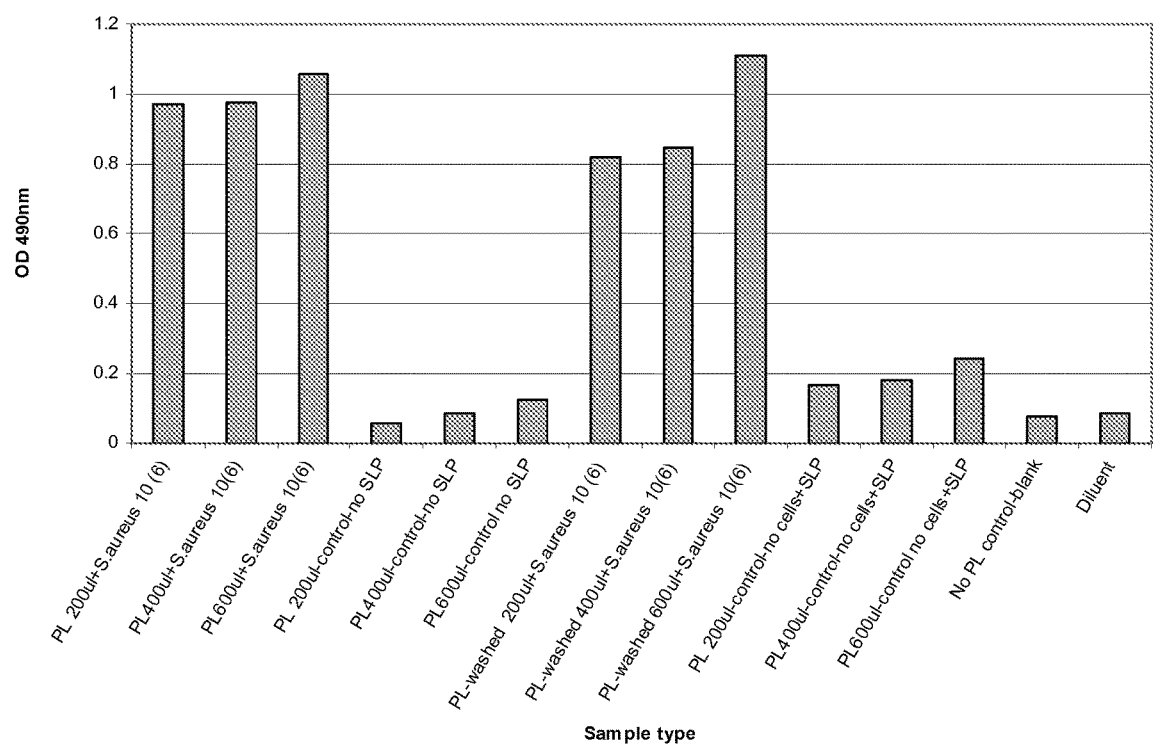
FIG. 23 is a graph showing an analysis of the effect of platelet volume on sensitivity for detection of spiked bacterial cells using alkaline extraction.

Example 13: Demonstration that Alkaline-Extraction Procedure Eliminates Effect of Inhibitory Factors in Platelet Preparations Aliquots of platelet preparation, 200 µl, 400 µl, and 600 µl were diluted 10 times with water and centrifuged at 14,000 rpm for 5 minutes. The same volumes of platelet were centrifuged in parallel without dilution with water. Platelet pellets were resuspended in 140 µl diluent. A small volume of *S. aureus* suspension was added into appropriate tubes to concentration 10(6) cells/ml. For extraction, 42 µl 10.2N sodium hydroxide was added and tubes were incubated at 70° C. for 10 minutes. Extraction was stopped with 48 µl 10.2M MES. 50 µl neutralized samples were transferred into tubes with 50 µl reconstituted SLP reagent containing DOPA. 10 µl 50 mM MBTH solution was added into each tube and incubated at 37° C. for 60 minutes. Reactions were stopped by adding 50 µl 10 mM PTU. FIG. 23 shows that alkaline extraction procedure worked well for extracting various amounts of platelets at concentrations which significantly exceed the concentration in the original platelet preparation. Removal of plasma from platelet preparation before extraction using centrifugation of diluted platelets does not improve detection indicating that the extraction efficiently eliminates activity of plasma inhibitory factors.

Example 14: Preparation of a Detection Reagent Containing Co-Lyophilized SLP Reagent, SLP Substrate and, MBTH Lyophilizing the SLP reagent, SLP substrate and MBTH to make one detection reagent produces a dry reagent that only need be added to an aqueous-based solution to detect bacterial or fungal contaminants. For example, detecting bacterial contaminants in platelets may be accomplished by adding an aliquot of alkali-extracted and neutralized platelets to a co-lyophilized SLP-DOPA-MBTH dry detection reagent to an aliquot of alkali-extracted and neutralized platelets as described in Assay Method 1. The reaction mixture is incubated, terminated by adding a stop reagent, and measured by detecting the colored reaction products spectrophotometrically as described in Assay Method 1.

To prepare the SLP-DOPA-MBTH dry detection reagent, one vial of dry SLP reagent containing DOPA (Wako Chemicals Inc.) was dissolved in 400 µl of 2 mM MBTH solution. The mixture was frozen in liquid nitrogen and the lyophilized under a vacuum.

Figure 24:
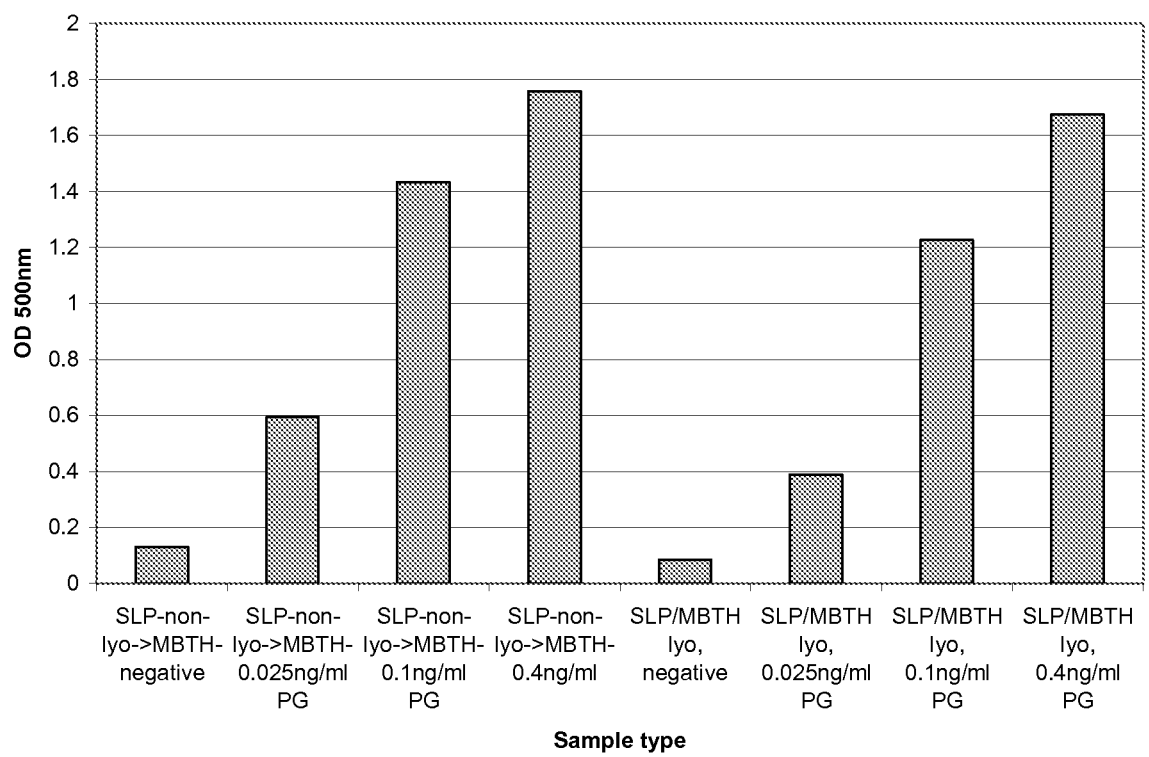
FIG. 24 is a graph showing the sensitivity of detection using the SLP-DOPA-MBTH dry detection reagent.

FIG. 24 demonstrates the SLP-DOPA-MBTH dry detection reagent retains the activity of the original SLP reagent containing DOPA in Assay Method 1. Extracted platelets were spiked with PG. Either the SLP-DOPA-MBTH dry detection reagent ("SLP/MBTH lyo") or SLP-DOPA and non-lyophilized MBTH ("SLP-non-lyo→MBTH") were added in concentrations of 0.025 ng/ml, 0.1 ng/ml, and 0.4 ng/ml. After incubating for 30 min at 30° C., a stop reagent (PTU-sodium dodecylsulfate) was added and a spectrophotometric reading (500 nm) was done directly in glass reaction tubes.

Example 15: Preparation of a Stop Reagent Containing an Anionic Detergent in Combination with a Phenoloxidase Inhibitor Using a phenoloxidate inhibitor-anionic detergent stop reagent stabilizes the SLP/MBTH reaction products while simultaneously reducing background absorbance (a light-scattering artifact) originating from partially solubilized platelet components. Reduction of this light-scattering artifact obviates the need to correct for the background absorbance using a second reference measurement (650 nm). Accordingly, the SLP/MBTH reaction products may be measured directly spectrophotometrically at 490-510 nm. Further, the original absorbance of SLP/MBTH reactions terminated with the PTU-lithium dodecylsulfate is preserved for a longer period than SLP/MBTH reactions terminated with PTU alone.

Figure 25:
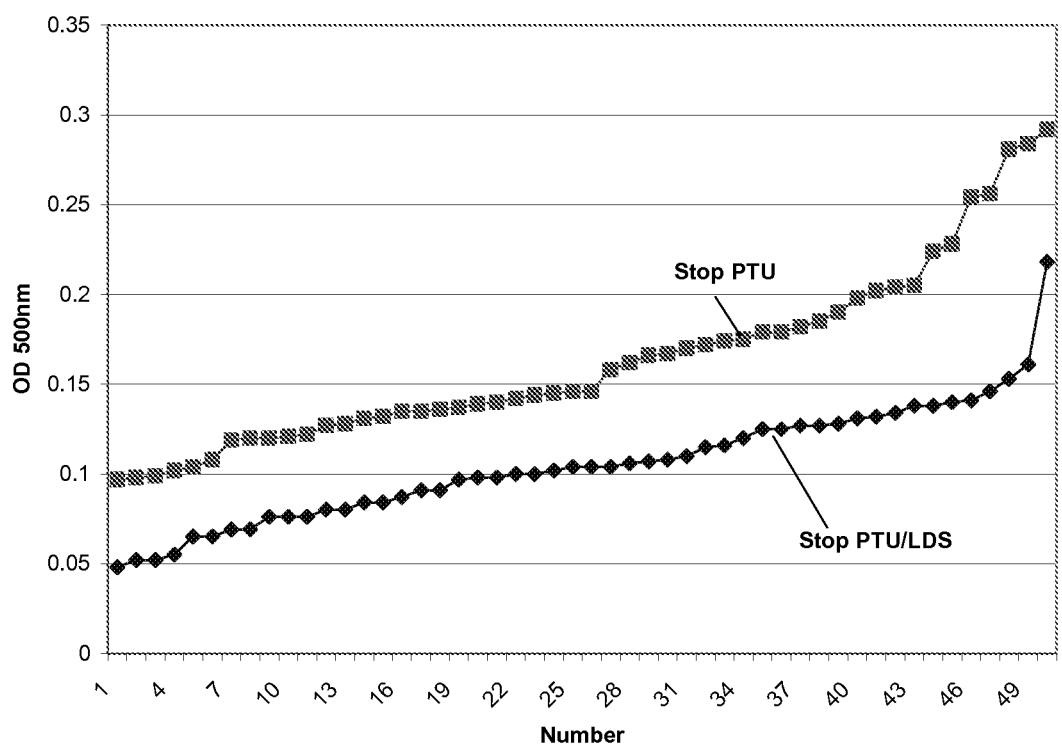
FIG. 25 is graph showing a demonstration of the ability to use the stop reagents PTU or PTO in combination with lithium dodecylsulfate.

A stop reagent containing 1 mM PTU and 2% lithium dodecylsulfate was prepared by dissolving 15.2 mg PTU in 80 ml water and adding 20 ml of 20% (in water) lithium dodecylsulfate solution. FIG. 25 demonstrates the effectiveness of the PTU-lithium dodecylsulfate stop reagent SLP/MBTH test in a reduction of absorbance inn negative samples in which the reaction was carried out for 35 min at room temperature and a spectrophotometric reading (500 nm) was done directly in glass reaction tubes.

Example 16: Detection of Urinary Tract Infections by Hemolymph-Based Assay

The following example shows the feasibility of using the hemolymph-based assay technology for detecting particular bacteria in urine to diagnose urinary tract infections (UTIs). Methods were evaluated on urine samples which had been either spiked with *E. coli* bacteria to resemble urine samples from UTI patients, or not spiked to serve as controls. *E. coli* strain ATCC25922 from the American Type Culture Collection was used in spiking experiments. To prepare the stock *E. coli* cultures, 15 ml of TSB media were inoculated with a stationary phase culture of *E. coli* (150 μl), and the culture was allowed to grow for approximately 4 hours (at 37° C. with shaking) to mid-log phase. The culture was then placed in the refrigerator to halt further growth and the titer was determined by serial plating on TSA plates. For the experiments described below, the concentration of the *E. coli* stock was 2E8 CFU/mL. In the first experiment, 10 μl of *E. coli* at 2E8 CFU/ml were added to 1 ml of urine, resulting in a concentration of 2E6 CFU/mL. In the second experiment, 300 of 2E8 *E. coli* were added to 3 ml of sample, resulting in a similar spiked concentration of 2E6 CFU/mL.

Figure 26:
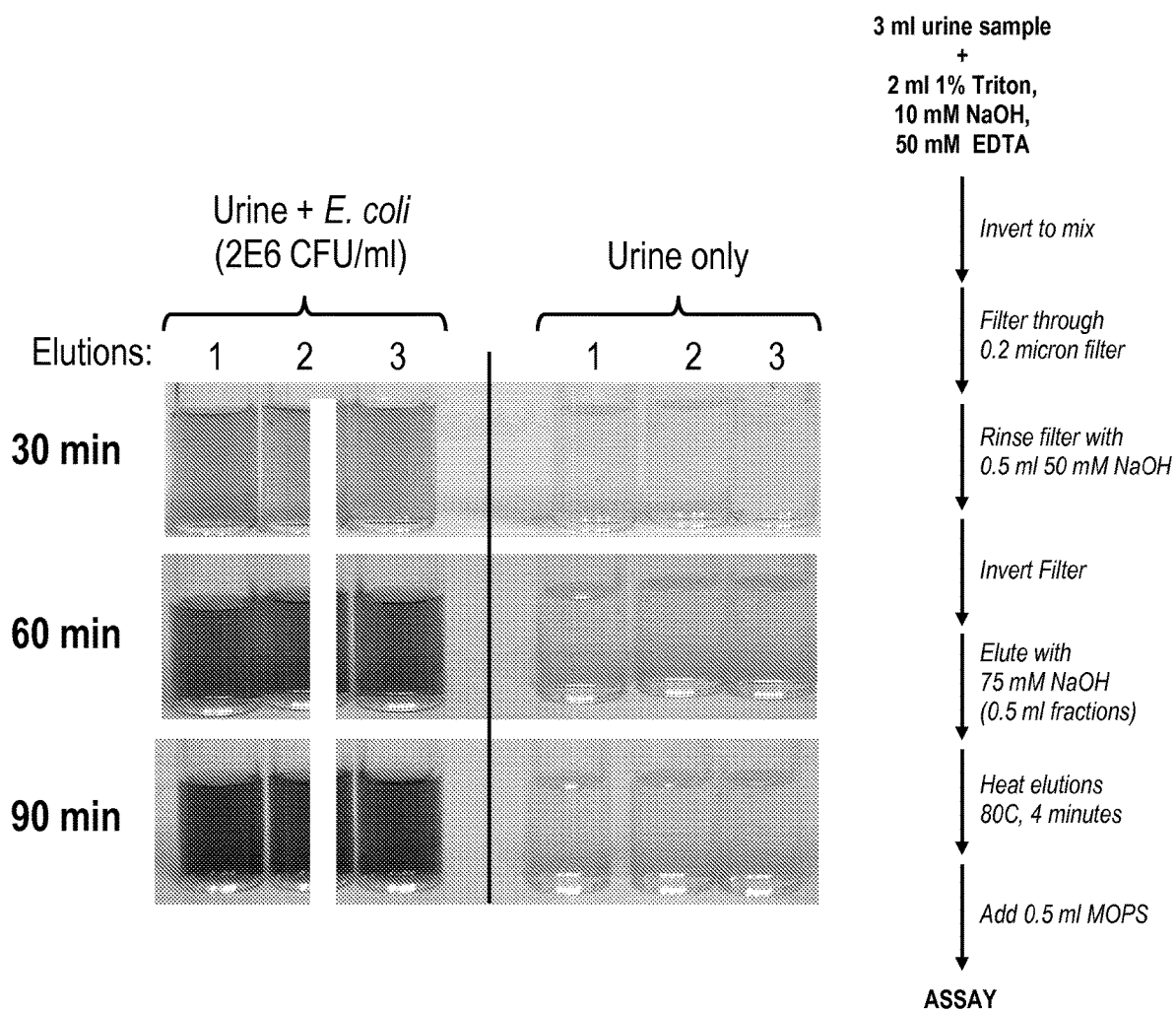
FIG. 26 shows the method and results of Experiment 1 from Example 16.

In the first method (Experiment 1; FIG. 26), several milliliters of urine were combined with an alkaline detergent solution (1% Triton X-100, 50 mM EDTA, 10 mM NaOH). This mixture was then filtered through a 0.2 micron syringe filter (typically polyethersulfone), which traps the bacteria. A small volume of alkaline rinse solution (50 mM NaOH) was flushed through the filter, to rinse away any artifactually reactive metabolites. Alkaline extraction solution (75 mM NaOH) was back-flushed through the filter, eluting the bacteria trapped on the surface of the filter. The eluted bacteria were heated at 80° C. for several minutes and then combined with an equal volume of neutralization solution (150 mM MOPS). A small volume (typically 0.3 ml) of this neutralized sample was added directly to an assay tube containing the lyophilized BacTx™ reagents (lyophilized hemolymph from *Manduca sexta*, dopamine, lysostaphin and a separate lyophilized pellet containing MBTH, trehalose, and Ficoll). The BacTx™ reagents consist of lyophilized hemolymph from *Manduca sexta*, dopamine, lysostaphin and a separate lyophilized pellet containing MBTH, trehalose, and Ficoll. In the presence of bacterial peptidoglycan, the hemolymph proteolytic enzyme cascade is triggered, resulting in the oxidation of dopamine to quinones which form a bright red adduct with MBTH. An increase in absorbance at approximately 500 nm over time, e.g. in 1-90 minutes, is thus an indication of bacteria in the urine sample. In this experiment, a urine sample which had been spiked with 2E6 CFU/ml of *E. coli* prior to the assay yielded a readily observed bright red color which intensifed over a 90 minute period, while a normal, unspiked urine sample yielded no color development (see Results below).

Figure 27:
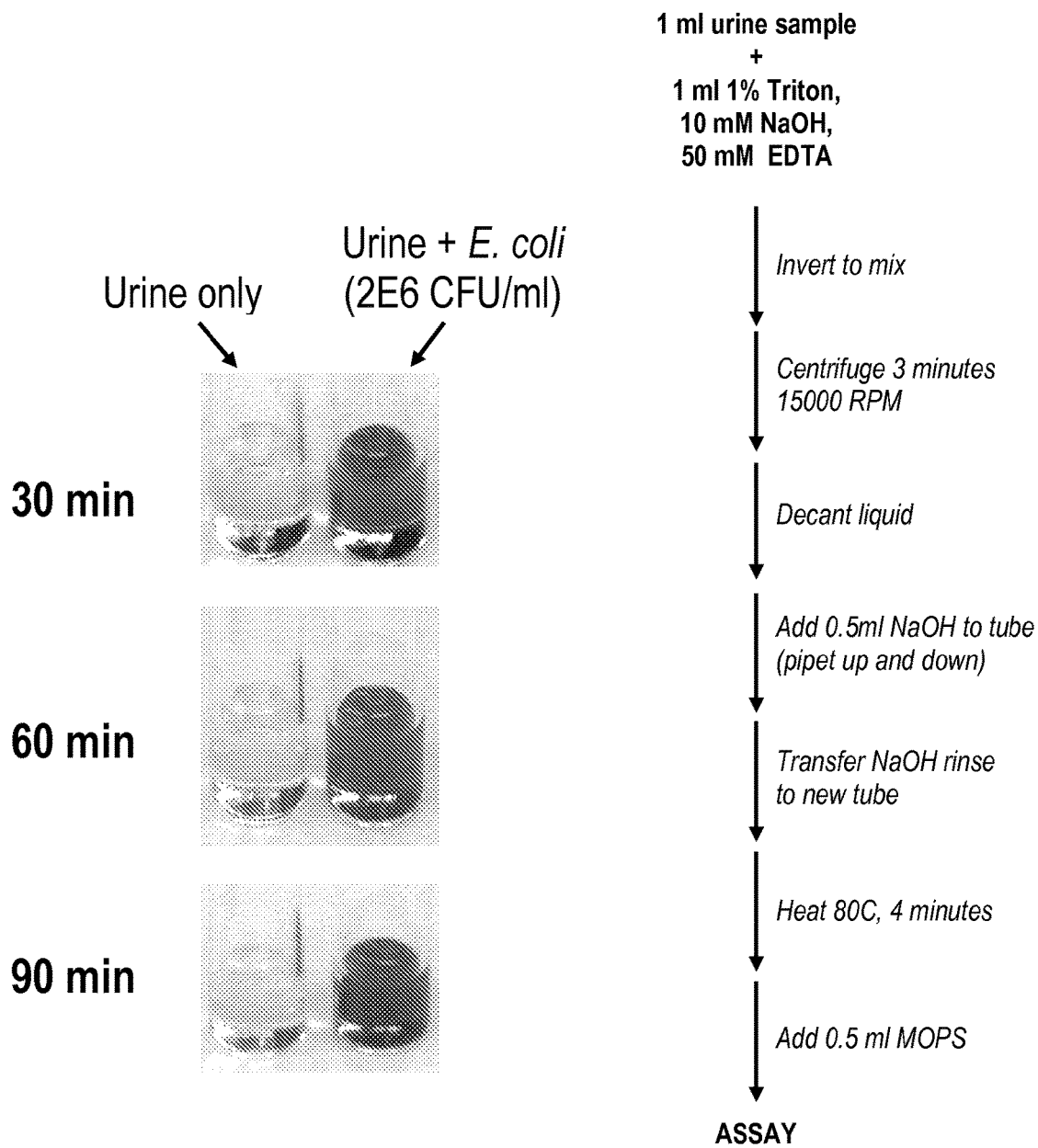
FIG. 27 shows the method and results of Experiment 2 from Example 16.

In the second method (Experiment 2; FIG. 27), one milliliter of urine sample was first combined with an alkaline detergent solution (1% Triton X-100, 50 mM EDTA, 10 mM NaOH), which inactivates artifactually reactive metabolites present in urine. This mixture was then centrifuged at 20,000×g for several minutes with a benchtop microcentrifuge, to pellet the bacteria. The liquid was decanted from the tube and the bacteria were re-suspended with an alkaline extraction solution (75 mM NaOH). This suspension was then heated at 80° C. for several minutes to lyse the bacteria, and then combined with a neutralization solution (150 mM MOPS). A small volume (typically 0.3 ml) of this neutralized sample was added directly to an assay tube containing the lyophilized BacTx™ reagents. The presence of bacteria was indicated by the change in color from green to red as described above. A urine sample spiked with 2E6 CFU/ml of *E. coli* bacteria before the assay generated a bright red-colored solution when tested, while a similar, unspiked urine sample remained clear for the 90 minute testing period (see FIGS. 26 and 27).

Example 17: BacTx™ Test for Cerebrospinal Fluid (CSF)

A promising application of the BacTx™ assay technology is detection of bacteria in CSF for diagnosis of bacterial meningitis. Feasibility of this application has been successfully demonstrated with two different sample preparation platforms.

Figure 28:
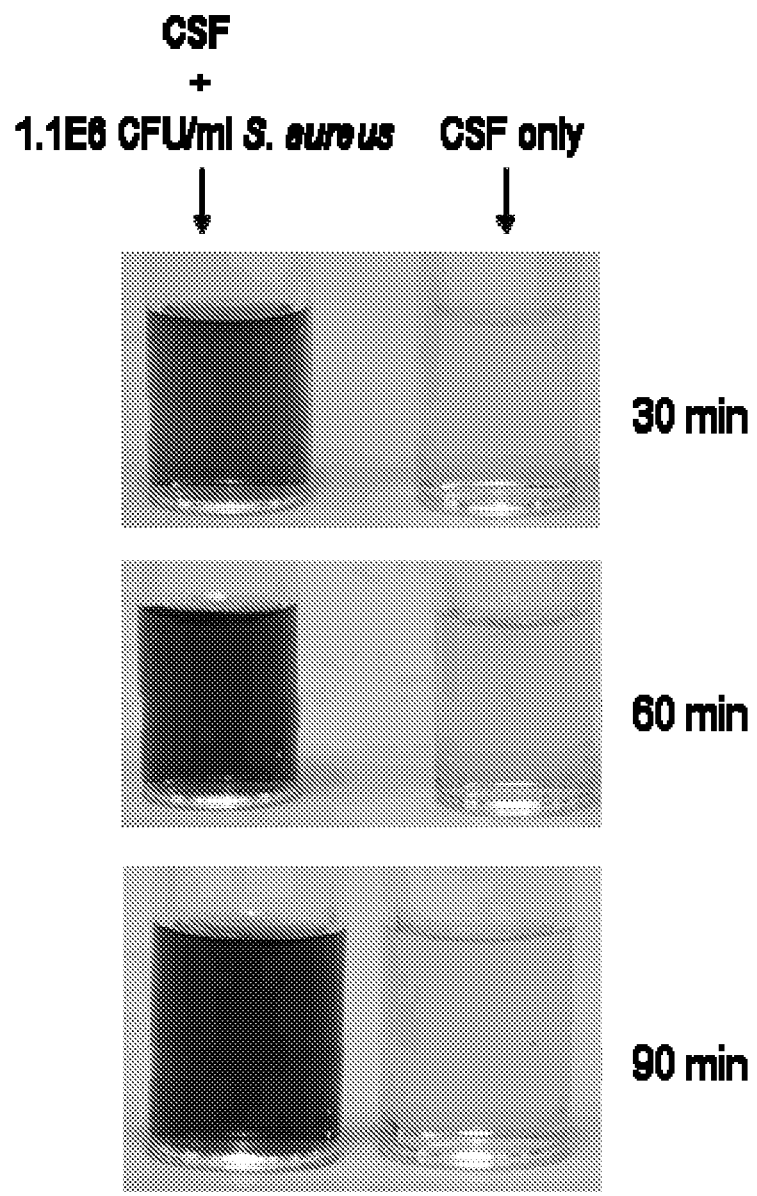
FIG. 28 shows BacTx testing of cerebrospinal fluid (CSF) with or without *Staphylococcus aureus*. CSF samples were processed using centrifugation method outlined in Scheme 1. 1E6 CFU/ml *S. aureus* was readily detected within 30 minutes.
Figure 29:
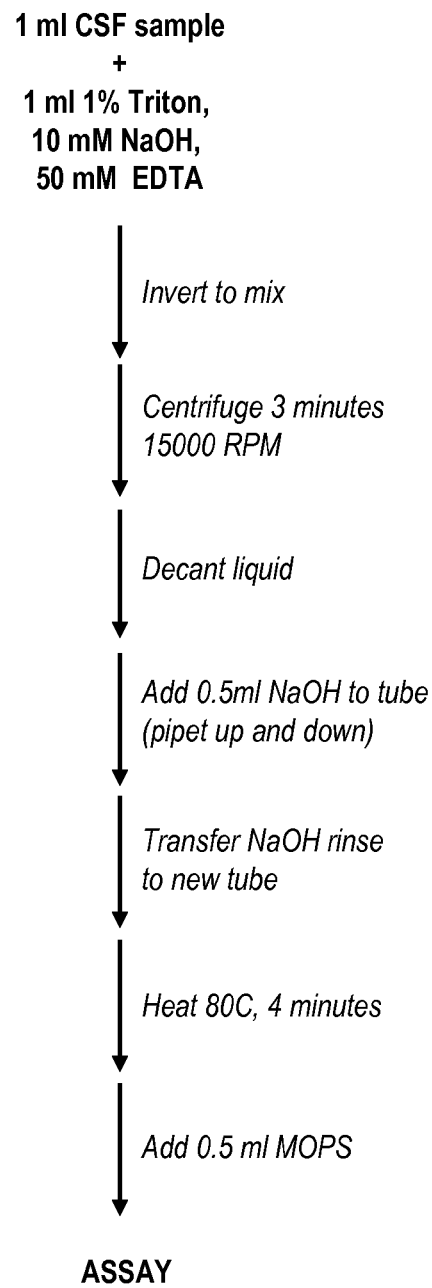
FIG. 29 depicts Scheme 1 for sample preparation of CSF samples prior to BacTx test using centrifugation.

In the first method (FIG. 29), one milliliter of CSF sample (from a 51 year old male) was first combined with an alkaline detergent solution (1% Triton X-100, 50 mM EDTA, 10 mM NaOH), which inactivates artifactually reactive metabolites present in CSF. This mixture was then centrifuged at 20,000×g for several minutes with a benchtop microcentrifuge, to pellet the bacteria. The liquid was decanted from the tube and the bacteria were re-suspended with an alkaline extraction solution (75 mM NaOH). This solution was then heated at 80° C. for several minutes to lyse the bacteria, and then combined with a neutralization solution (150 mM MOPS). A small volume (typically 0.3 ml) of this neutralized sample was added directly to an assay tube containing the lyophilized BacTx™ reagents. The BacTx™ reagents consist of a lyophilized cake of hemolymph from *M. sexta*, dopamine, and lysostaphin and a separate lyophilized pellet containing MBTH, trehalose, and Ficoll. A color change from green to red within a defined period of time, for instance 30-90 minutes in this example, indicates that bacteria are present in the CSF sample (FIG. 28).

Figure 30:
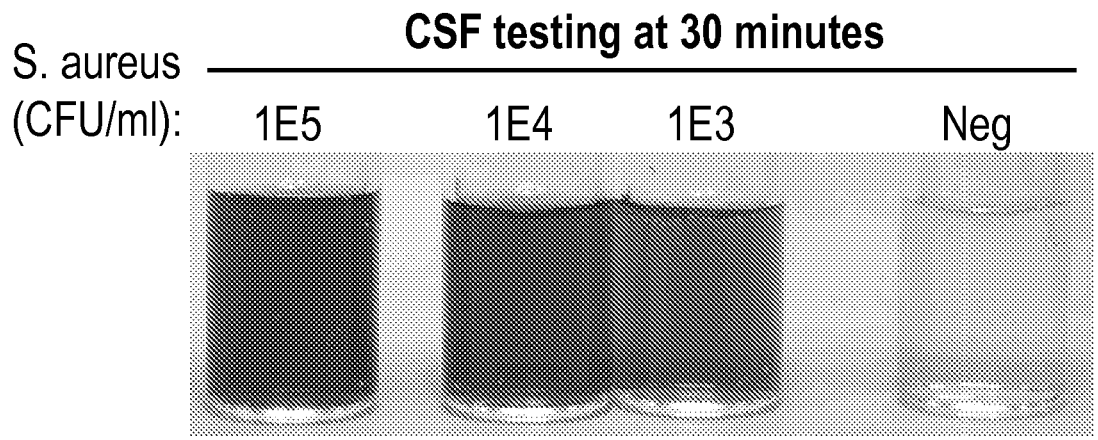
FIG. 30 shows sensitivity of BacTx assay of *S. aureus* in CSF. CSF samples containing 1E5, 1E4, 1E3 CFU/ml, or no *S. aureus* were processed using sample preparation outlined in Scheme 1. *S. aureus* concentration of 1E3 CFU/ml was detected within 45 minutes (A). Kinetic analysis of assays indicate that 1E5 CFU/ml *S. aureus* glucan, was detected (A500>0.5) in less than 10 minutes, 1E4 CFU/ml in less than 20 minutes, and 1E3 CFU/ml in less than 35 minutes (B).
Figure 30:
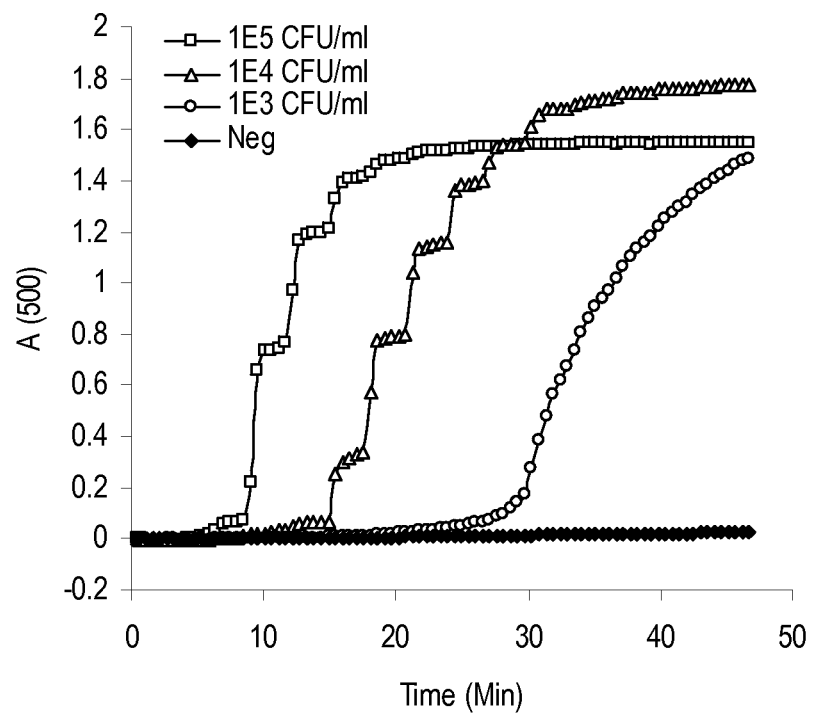
Figure 31:
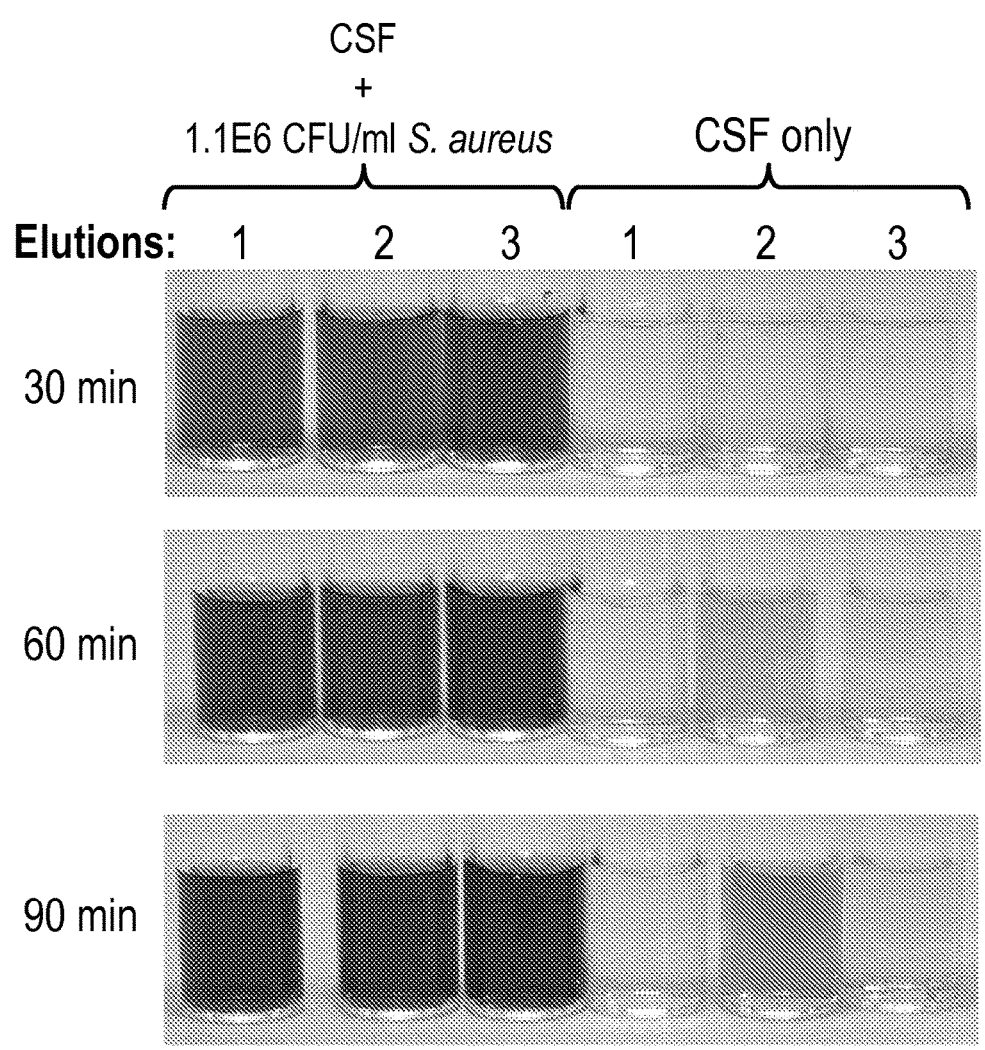
FIG. 31 shows BacTx testing of CSF with or without *Staphylococcus aureus*. CSF samples were processed using filtration method outlined in Scheme 2. 1E6 CFU/ml *S. aureus* was readily detected within 30 minutes.
Figure 32:
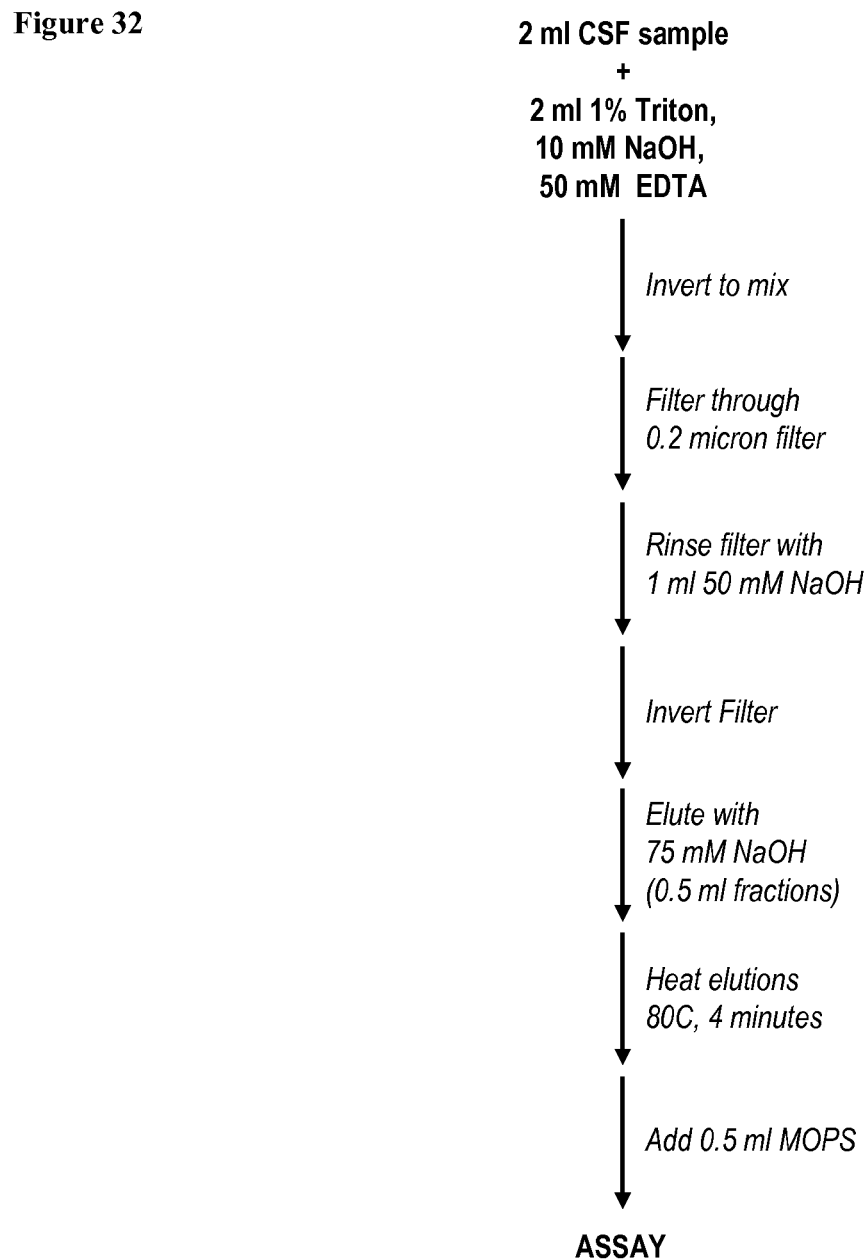
FIG. 32 shows Scheme 2 for sample preparation of CSF samples prior to BacTx test using filtration.

In the second method (FIG. 32), 2 milliliters of CSF were combined with an alkaline detergent solution (1% Triton X-100, 50 mM EDTA, 10 mM NaOH). This mixture was then filtered through a 0.2 micron syringe filter (typically polyethersulfone), which traps the bacteria. A small volume of alkaline rinse solution (50 mM NaOH) was flushed through the filter, to rinse away any artifactually reactive metabolites. Alkaline extraction solution (75 mM NaOH) was back-flushed through the filter, eluting the bacteria trapped on the surface of the filter. The eluted bacteria were heated at 80° C. for several minutes and then combined with an equal volume of neutralization solution (150 mM MOPS). A small volume (typically 0.3 ml) of this neutralized sample was added directly to an assay tube containing the lyophilized BacTx™ reagents (described above). The presence of bacteria was indicated by the change in color from green to red within a defined period of time, e.g. 30-90 minutes in this example. (FIGS. 30, 31). In this experiment, *Staphylococcus aureus* bacteria spiked into a CSF sample could be readily detected within 30 minutes at concentrations from 1E5 CFU/ml down to 1E3 CFU/ml. As indicated by the kinetic trace of absorbance at 500 nm obtained from a photometer monitoring the reaction, the lag time preceding the rise in absorbance is inversely proportional to the concentration of bacteria in the sample (FIG. 30 A,B). Thus, at the highest concentration of bacteria (1E5 CFU/ml) in this experiment, a rise in absorbance could be detected well before 30 minutes had elapsed, and in fact within about 10 minutes. An estimate of bacterial concentration in the sample can therefore be derived from measuring the amount of time elapsed from addition of enzyme substrate until development of measurable absorbance in the reaction tube. A standard curve showing bacterial concentration vs. time to reach a certain absorbance can be used for quantitative estimation of the bacterial concentration in a sample that has been tested with this method.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for detecting peptidoglycan, β-glucan, bacteria, bacterial fragments, or fungi in a sample, comprising steps of:
   (a) providing the sample;
   (b) providing reagents, comprising:
      (i) a hemolymph from a lepidopteran insect;
      (ii) a phenoloxidase substrate; and
      (iii) 3-methyl-2-benzothiazolinone hydrazone or a derivative thereof having the general structure:

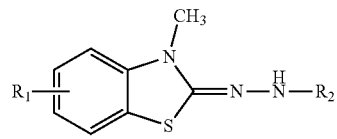

wherein $R_1$ represents H, alkyl, halide, $-NO_2$, $-CO_2$, or $-SO_3$;
   wherein $R_2$ represents H, or $-SO_2R_3$; and
   wherein $R_3$ represents alkyl, aryl, and heteroaryl;
   (c) combining the sample and reagents;
   (d) spectrophotometrically detecting a measurable absorbance in the combination,
   wherein when peptidoglycan, bacteria, bacterial fragments, ß-glucan, or fungi are present in the sample, a colored reaction product forms in the combination, and
   (e) quantifying the concentration of peptidoglycan, bacteria, bacterial fragments, ß-glucan, or fungi present in the sample, comprising steps of:
      determining the detected absorbance of the combination at a time elapsed from the step of combining to the step of detecting; and
      correlating with a standard curve having absorbance and concentration.

2. The method of claim 1, wherein the sample is a clinical sample, an environmental sample, an agricultural sample, a manufacturing sample, or a medical product.

3. The method of claim 2, wherein the sample is a clinical sample, which is an anesthetic, blood, a blood product, a dialysis fluid, a hydration fluid, an imaging agent, a nutrient fluid, a pharmacologically active agent, platelets, or a vaccine.

4. The method of claim 2, wherein the sample is selected from the group consisting of urine, a urine product, and cerebrospinal fluid.

5. The method of claim 1, wherein the sample is a suspension or a liquid.

6. The method of claim 5, further comprising a step of centrifuging the sample prior to the step of combining wherein bacteria or fungi present in the sample are pelleted during the centrifugation step.

7. The method of claim 1, wherein the phenoloxidase substrate is L-3,4-dihydroxyphenylalanine, dopamine, 3,4-dihydroxyphenyl propionic acid, 3,4-dihydroxyphenyl acetic acid, a dihydroxyphenol, a monophenol, or catechol.

8. The method of claim 1, further comprising the step of exposing the sample to an extraction solution at an elevated temperature, prior to the step (c).

9. The method of claim 8, wherein the extraction solution is an alkaline extraction solution.

10. The method of claim 8, further comprising the step of exposing the sample to a neutralization buffer prior to the step of combining the sample with the hemolymph from a lepidopteran insect, the phenoloxidase substrate that generates a quinone reaction product, and 3-methyl-2-benzothiazolinone hydrazone or derivative thereof.

11. The method of claim 1, wherein at least one of the provided reagents is in a lyophilized form.

12. The method of claim 1, further comprising the step of exposing the sample to a stop reagent.

13. The method of claim 12, wherein the stop reagent is an acid reagent, a phenoloxidase inhibitor, or a strong anionic detergent alone or in combination with a phenoloxidase inhibitor.

14. The method of claim 1, wherein the lepidopteran insect is selected from the group consisting of a hornworm, a silkworm, a flesh fly, a house fly, an Emmafield cricket and a beetle.

15. The method of claim 1, wherein the absorbance of the colored reaction product indicating the presence of bacteria is monitored continuously over time.

16. The method of claim 14, wherein the lepidopteran insect is hornworm or silkworm.

17. The method of claim 7, wherein the phenoloxidase substrate is dopamine.

* * * * *